(12) United States Patent
Sobinov et al.

(10) Patent No.: US 11,197,769 B2
(45) Date of Patent: Dec. 14, 2021

(54) SYSTEMS AND METHODS FOR APPROXIMATING MUSCULOSKELETAL DYNAMICS

(71) Applicants: West Virginia University, Morgantown, WV (US); University of Pittsburgh—Of the Commonwealth System of Higher Education, Pittsburgh, PA (US)

(72) Inventors: Anton Sobinov, Morgantown, WV (US); Sergiy Yakovenko, Morgantown, WV (US); Valeriya Gritsenko, Morgantown, WV (US); Matthew Boots, Morgantown, WV (US); Robert Gaunt, Pittsburgh, PA (US); Jennifer Collinger, Pittsburgh, PA (US); Lee Fisher, Pittsburgh, PA (US)

(73) Assignees: West Virginia University, Morgantown, WV (US); University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 16/722,815

(22) Filed: Dec. 20, 2019

(65) Prior Publication Data
US 2020/0253751 A1 Aug. 13, 2020

Related U.S. Application Data

(63) Continuation-in-part of application No. PCT/US2018/051575, filed on Sep. 18, 2018.
(Continued)

(51) Int. Cl.
*A61F 2/72* (2006.01)
*G06F 3/01* (2006.01)
(Continued)

(52) U.S. Cl.
CPC .............. *A61F 2/72* (2013.01); *A61F 2/582* (2013.01); *A61F 2/70* (2013.01); *G06F 3/011* (2013.01);
(Continued)

(58) Field of Classification Search
CPC . A61B 5/389; A61F 2/50; A61F 2/582; A61F 2/70; A61F 2/72; A61F 2002/0894;
(Continued)

(56) References Cited

U.S. PATENT DOCUMENTS

| | | | |
|---|---|---|---|
| 6,344,062 B1 * | 2/2002 | Abboudi | A61B 5/036 623/24 |
| 2004/0106881 A1 * | 6/2004 | McBean | A61B 5/389 601/5 |

(Continued)

FOREIGN PATENT DOCUMENTS

WO 2019056008 A1 3/2019

OTHER PUBLICATIONS

International Search Report and Written Opinion dated Mar. 16, 2021 for PCT Patent Application No. PCT/US20/66266.
(Continued)

*Primary Examiner* — Mihir K Rayan
(74) *Attorney, Agent, or Firm* — Thomas | Horstemeyer, LLP

(57) ABSTRACT

A system and method for controlling a device, such as a virtual reality (VR) and/or a prosthetic limb are provided. A biomimetic controller of the system comprises a signal processor and a musculoskeletal model. The signal processor processes M biological signals received from a residual limb to transform the M biological signals into N activation signals, where M and N are integers and M is less than N. The musculoskeletal model transforms the N activation signals into intended motion signals. A prosthesis controller
(Continued)

transforms the intended motion signals into three or more control signals that are outputted from an output port of the prosthesis controller. A controlled device receives the control signals and performs one or more tasks in accordance with the control signals.

21 Claims, 18 Drawing Sheets

Related U.S. Application Data

(60) Provisional application No. 62/559,711, filed on Sep. 18, 2017.

(51) Int. Cl.
*A61F 2/58* (2006.01)
*G16H 30/20* (2018.01)
*A61F 2/70* (2006.01)
*A61F 2/68* (2006.01)
*A61F 2/08* (2006.01)
*A61B 5/389* (2021.01)

(52) U.S. Cl.
CPC .............. *G06F 3/015* (2013.01); *G16H 30/20* (2018.01); *A61B 5/389* (2021.01); *A61F 2002/0894* (2013.01); *A61F 2002/6827* (2013.01); *A61F 2002/704* (2013.01)

(58) Field of Classification Search
CPC ........ A61F 2002/6827; A61F 2002/704; B25J 9/16; G06F 3/011; G06F 3/015; G16H 30/20; G16H 50/50
See application file for complete search history.

(56) References Cited

U.S. PATENT DOCUMENTS

| | | | |
|---|---|---|---|
| 2010/0324699 A1* | 12/2010 | Herr | A61F 5/0127 623/27 |
| 2011/0307079 A1* | 12/2011 | Oweiss | A61B 5/4094 623/27 |
| 2013/0310979 A1* | 11/2013 | Herr | B62D 57/032 700/258 |
| 2014/0364723 A1 | 12/2014 | Meyer et al. | |
| 2016/0207201 A1 | 7/2016 | Herr et al. | |
| 2017/0266019 A1 | 9/2017 | Farina et al. | |
| 2017/0360578 A1 | 12/2017 | Shin et al. | |
| 2020/0042094 A1* | 2/2020 | Ang | G06F 3/0485 |
| 2020/0265943 A1* | 8/2020 | Sobinov | B25J 9/16 |

OTHER PUBLICATIONS

Delp, Scott L., et al. "OpenSim: open-source software to create and analyze dynamic simulations of movement." IEEE transactions on biomedical engineering 54.11 (2007): 1940-1950.

Menegaldo, Luciano Luporini; et al. "A 'cheap' optimal control approach to estimate muscle forces in musculoskeletal systems." Journal of biomechanics 39.10 (2006): 1787-1795.

Sartori, Massimo, et al. "Estimation of musculotendon kinematics in large musculoskeletal models using multidimensional B-splines." Journal of biomechanics 45.3 (2012): 595-601.

International Search Report and Written Opinion dated Jan. 4, 2019 for PCT Patent Application No. PCT/US2018/051575.

Chadwick, Edward K., et al. "A real-time, 3-D musculoskeletal model for dynamic simulation of arm movements." IEEE Transactions on Biomedical Engineering 56.4 (2008): 941-948.

Kurse, Manish U; et al. "Extrapolatable analytical functions for tendon excursions and moment arms from sparse datasets." IEEE transactions on biomedical engineering 59.6 (2012): 1572-1582.

* cited by examiner

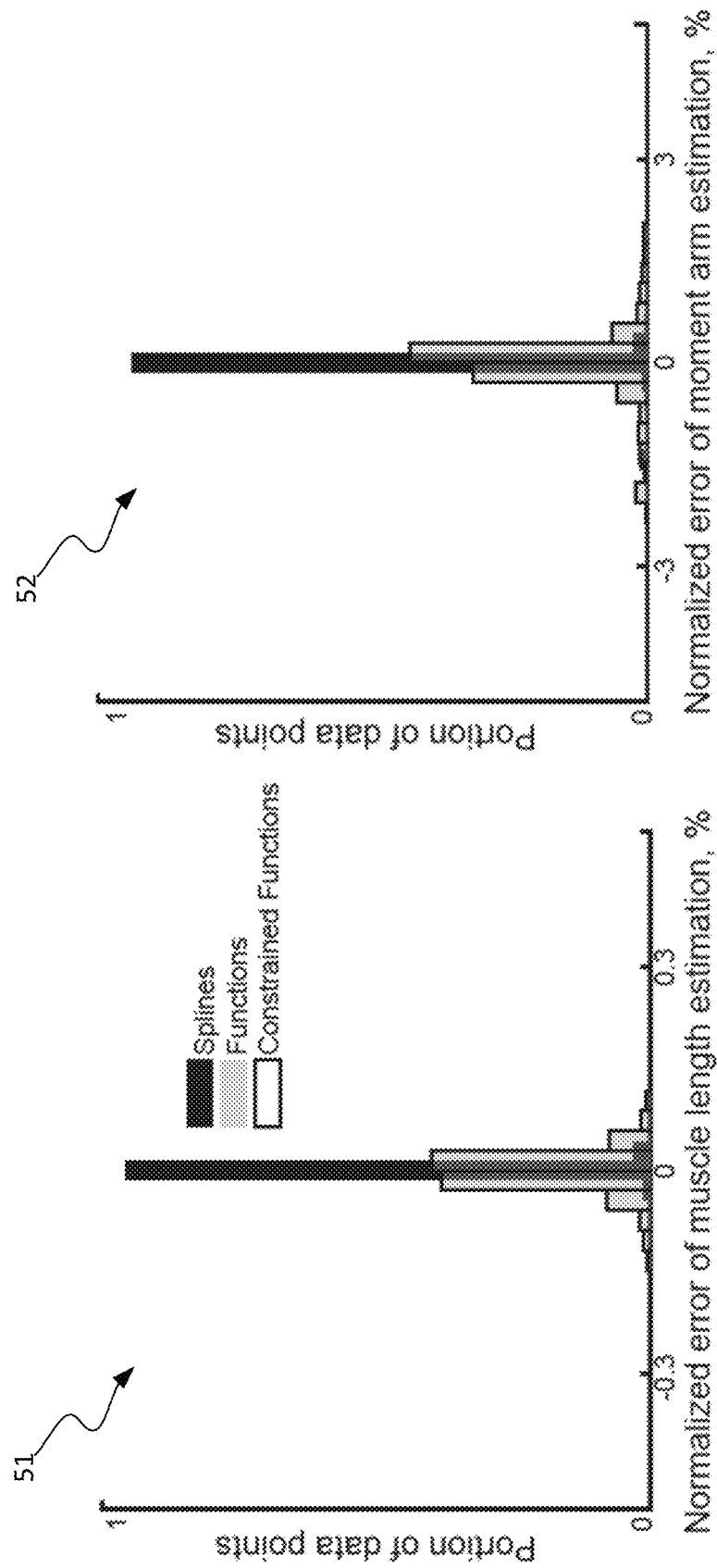

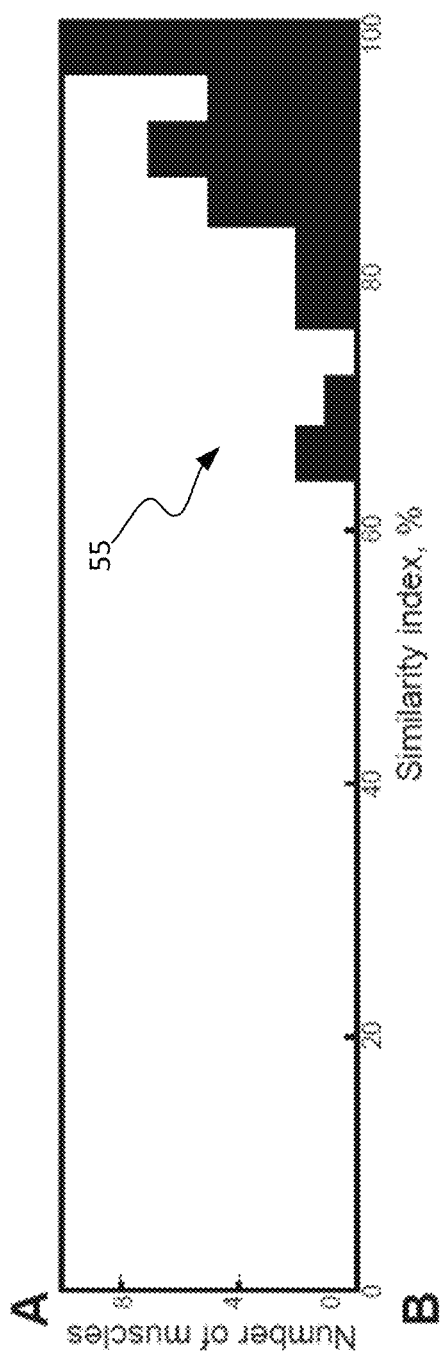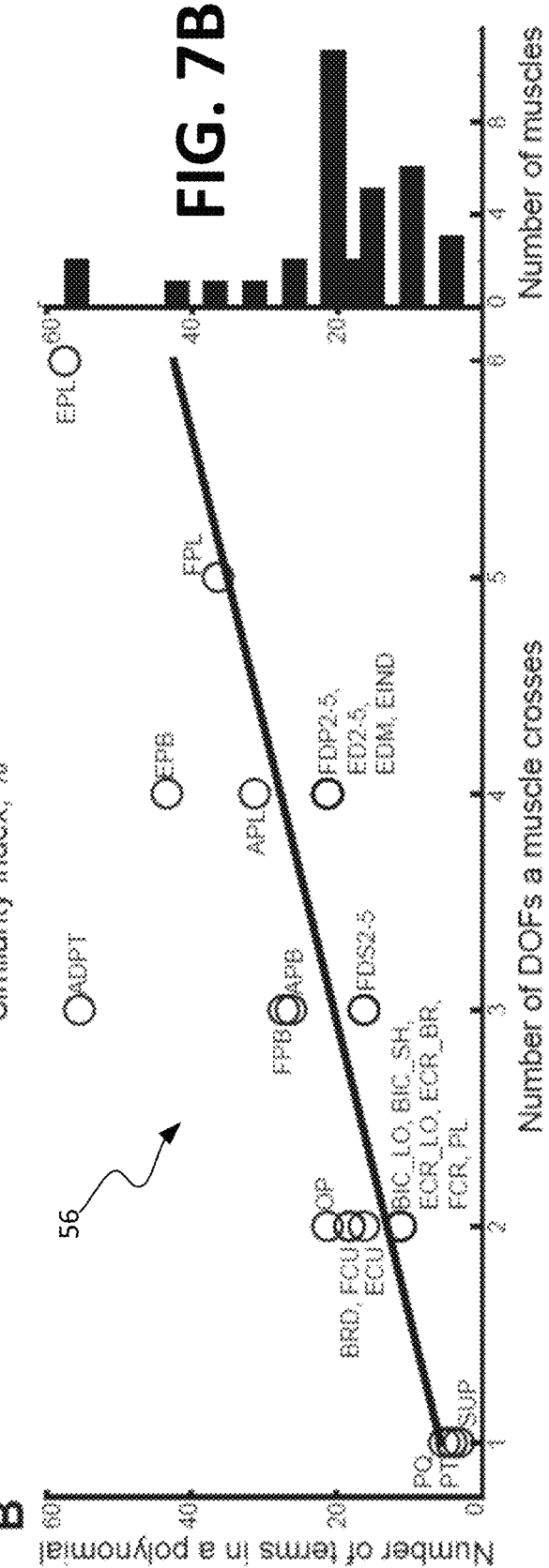

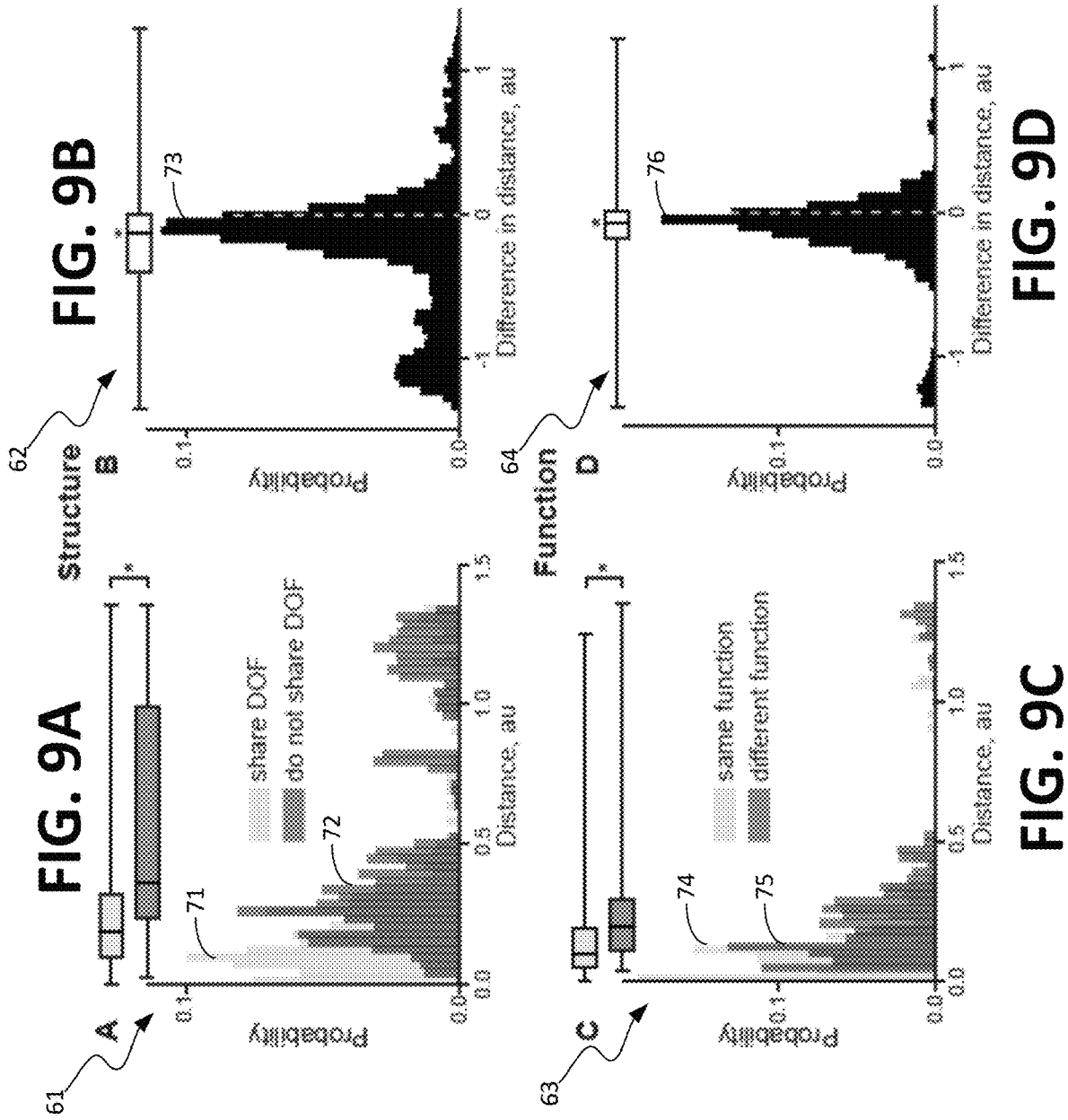

SYSTEMS AND METHODS FOR APPROXIMATING MUSCULOSKELETAL DYNAMICS

CROSS-REFERENCE TO RELATED APPLICATIONS

This application is a PCT international application that claims priority to a continuation-in-part (CIP) application filed on Dec. 20, 2019, entitled "SYSTEMS AND METHODS FOR APPROXIMATING MUSCULOSKELETAL DYNAMICS" having U.S. application Ser. No. 16/722,815, which is CIP of PCT international application number PCT/US2008/051575 filed on Sep. 18, 2018, entitled "SYSTEMS AND METHODS FOR APPROXIMATING MUSCULOSKELETAL DYNAMICS," which claims priority to and the benefit of the filing date of a U.S. provisional application having Ser. No. 62/559,711, filed on Sep. 18, 2017, entitled "APPROXIMATION OF COMPLEX MUSCULOSKELETAL DYNAMICS," both of which are hereby incorporated by reference herein in their entireties.

GOVERNMENT SUPPORT

This invention was made with support from the Department of Defense under contract No. W911NF-15-2-0016. The Government has certain rights in this invention.

FIELD OF THE INVENTION

The present invention generally relates to prosthetics, and more particularly, to systems and methods for controlling prosthetics, orthotics, virtualized biological appendages with and without assistive devices.

BACKGROUND OF THE INVENTION

Prosthetic devices help restore functionality in patients who suffer from limb loss. Access to prosthetics results in a variety of benefits including reduced pain, enhanced social interaction, decreased dependence on caregivers, and a renewed opportunity to become productive members of society. Choosing a prosthetic option depends on a person's level of limb loss and their goals for using a prosthesis.

A goal of prosthetic devices is to mimic as close as possible human motion. A key parameter is the number of available degrees of freedom (DOFs) in the device. For example, the human arm, excluding the hand, has five to seven general DOFs: three DOFs in the shoulder, allowing the arm to pivot with pitch, yaw, and roll; one DOF along the elbow for yaw; and three DOFs along the wrist for yaw, pitch, and roll. The hand has additional DOFs that can be defined based on the complexity of movement. Hand DOFs range from one, where all fingers move together to open and close the hand, to twenty where each finger joint can move independently. In designing a prosthetic arm, it is imperative to keep these DOFs in mind to optimize motion in conjunction with dexterity and mobility. The more proximal the amputation and the more functionality that needs to be restored, the more DOFs in the prosthetic device, and consequently, the complexity of the system increases.

Robotic prostheses convert biological signals from the user into motion of the prosthesis. At the forefront of this technology is the myoelectric prosthetic. Such devices convert muscle activity in the residual limb into control signals for the prosthesis with the aim to restore biologically accurate functions. Myoelectric control of prosthetics is currently supported by prostheses manufacturers and affiliated companies.

Despite technological advances in prosthetic design, myoelectric prostheses can be difficult to control. The forethought required to operate this type of device in a complex way can be quite burdensome. This can lead to passive-use of the device, which can have detrimental effects on the contralateral limb due to overuse. Moreover, several studies suggest an increased rate of rejection of myoelectric prostheses with lengthened follow-up. Providing extensive training as well as intuitive and robust control for myoelectric prostheses may reduce injuries and increase usability.

Once a patient is fitted with a prosthetic device, its success is based on its usefulness in everyday life. However, the prosthetic abandonment rate has not decreased even as technology has improved. The technology to enable a prosthetic device to move and feel precisely like a biological limb introduces increased complexity to the device. The high cognitive load required to operate these devices can be distracting and tiring.

Several groups have started the development of a virtual reality system that helps amputees learn to use their new prosthetic limbs. Biomechanical simulation tools have been developed for real-time feedback. Separately, musculoskeletal and mechanical modeling has been done to improve control of complex prosthetics. In addition, the prosthesis itself was manufactured to represent the musculoskeletal transformation within its design. However, the use of these simulations in virtual reality before their use by patients has not yet been demonstrated. Other systems have been developed to use virtual reality and neural stimulation to help change an amputee's phantom limb to more closely match their prosthetic limb, making it easier and more natural to use. These systems are designed to promote embodiment of the device, so that it feels as if it is a part of the user's body. They are not designed to optimize the control of the prosthesis.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

FIGS. 6A and 6B illustrate histograms of the normalized error in estimation of muscle lengths and moment arms, respectively, using splines and optimized polynomials with and without the aforementioned constraint associated with steps 11-13 of FIG. 4.

FIG. 7A illustrates a graph of similarity index (SI) between polynomials composed with and without the differential relationship between length and moment arms of each muscle, which illustrates that the compositions are similar.

FIG. 7B illustrates a graph of the number of joints the muscle spans vs. the number of terms in the approximating polynomials, which demonstrates that the number of terms increases with the number of joints the muscle spans.

FIG. 9A is a graph showing two probability density distributions of muscle vector distances for muscles with and without shared anatomical DOFs. The asterisks indicate $p<10^{-8}$ in statistical comparisons with $\alpha=0.05$.

FIG. 9B is a graph showing the difference between the distributions in FIG. 9A. The asterisk indicates $p<10^{-8}$ in a statistical comparison to zero with $\alpha=0.05$.

FIG. 9C is a graph showing two probability density distributions of muscle vector distances for muscles sharing spanning at least one the same DOF and belonging to two different functional groups, e.g., flexors and extensors.

FIG. 9D is a graph showing the difference between the distributions in FIG. 9C.

DETAILED DESCRIPTION

Figure 1:
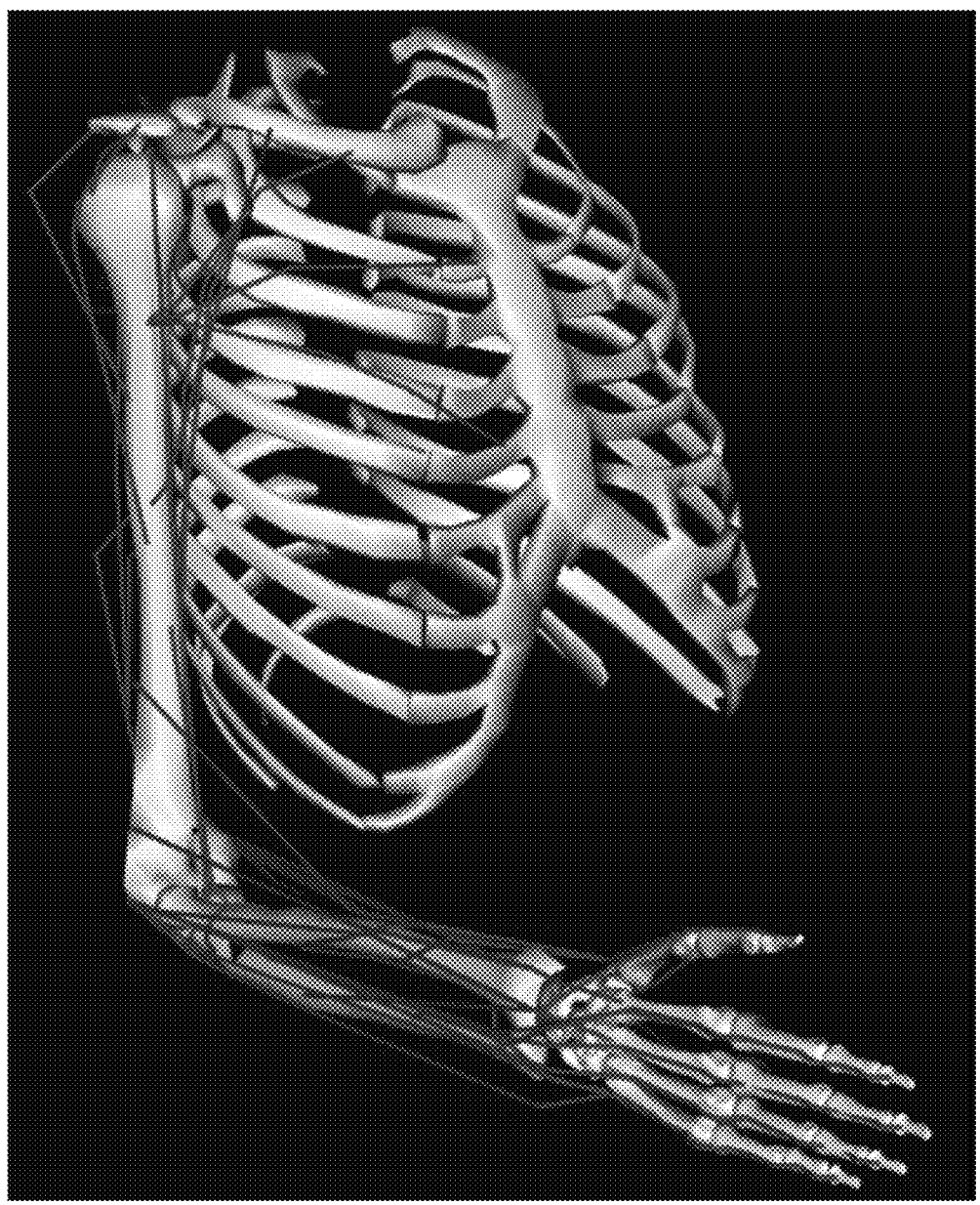
FIG. 1 is an OpenSim model of an upper limb of a human arm having various musculotendon actuators.

Representative embodiments of the present disclosure are directed to various embodiments of a system and method for controlling a device, such as a virtual reality (VR) and/or a prosthetic limb. In accordance with an embodiment, a biomimetic controller of the system comprises a signal processor and a musculoskeletal model. The signal processor processes M biological signals received from a residual limb to transform the M biological signals into N activation signals, where M and N are integers and M is less than N. The musculoskeletal model transforms the N activation signals into intended motion signals. A prosthesis controller transforms the intended motion signals into control signals that are outputted from an output port of the prosthesis controller. A controlled device receives the control signals and performs one or more tasks in accordance with the control signals.

The above-referenced PCT international application number PCT/US2008/051575 (hereinafter referred to as "the parent application"), which is the parent application of the present application, discloses, inter alia, an approximation method that includes the steps of acquiring or receiving an input dataset associated with muscle lengths and moment arms for a plurality of physiological postures of a body limb, preselecting respective polynomials that approximate the muscle moment arms and lengths, generating respective lists of one or more candidates for expanding each respective polynomial, selecting a respective candidate for expanding each polynomial based on respective estimates of which of the candidates is the most suitable candidate, expanding the respective polynomials by the respective selected candidates, determining whether further expansion of the polynomials is possible and would be sufficiently beneficial to warrant expansion. If so, the process returns to the step of generating respective lists of candidates for expansion followed by the step of selecting the respective suitable candidates. If not, the musculoskeletal dynamics of the limb are estimated based on the latest structure of the polynomials.

In accordance with a preferred embodiment, the approximation method disclosed in the parent application is performed to obtain the structures of the polynomials a priori. Then, in accordance with embodiments disclosed herein, the polynomial structures obtained are used in a biomimetic controller to estimate musculoskeletal dynamics in real-time or near-real time in order to simultaneously control multiple DOFs of some device, such as a real prosthesis device, for example.

For completeness, prior to describing representative embodiments in accordance with the inventive principles and concepts of the present disclosure, portions of the parent application are repeated herein with reference to FIGS. 1-9D of the parent application. Then, representative embodiments according to teachings of the present disclosure are described herein with reference to FIGS. 10-18C.

In the following detailed description, for purposes of explanation and not limitation, example embodiments disclosing specific details are set forth in order to provide a thorough understanding of an embodiment according to the present teachings. However, it will be apparent to one having ordinary skill in the art having the benefit of the present disclosure that other embodiments according to the present teachings that depart from the specific details disclosed herein remain within the scope of the appended claims. Moreover, descriptions of well-known apparatuses and methods may be omitted so as to not obscure the description of the example embodiments. Such methods and apparatuses are clearly within the scope of the present teachings.

The terminology used herein is for purposes of describing particular embodiments only, and is not intended to be limiting. The defined terms are in addition to the technical and scientific meanings of the defined terms as commonly understood and accepted in the technical field of the present teachings.

As used in the specification and appended claims, the terms "a," "an," and "the" include both singular and plural referents, unless the context clearly dictates otherwise. Thus, for example, "a device" includes one device and plural devices.

Relative terms may be used to describe the various elements' relationships to one another, as illustrated in the accompanying drawings. These relative terms are intended to encompass different orientations of the device and/or elements in addition to the orientation depicted in the drawings.

It will be understood that when an element is referred to as being "connected to" or "coupled to" or "electrically coupled to" another element, it can be directly connected or coupled, or intervening elements may be present.

The term "memory" or "memory device", as those terms are used herein, are intended to denote a non-transitory computer-readable storage medium that is capable of storing computer instructions, or computer code, for execution by one or more processors or controllers. References herein to "memory" or "memory device" should be interpreted as one or more memories or memory devices. The memory may, for example, be multiple memories within the same computer system. The memory may also be multiple memories distributed amongst multiple computer systems or computing devices.

A "controller," as that term is used herein, encompasses an electronic component that is able to execute a computer program or executable computer instructions. A controller may also refer to a collection of controllers. A controller may comprise one or more processors, such as, for example, a microprocessor or microcontroller.

Exemplary, or representative, embodiments will now be described with reference to the figures, in which like reference numerals represent like components, elements or features. It should be noted that features, elements or components in the figures are not intended to be drawn to scale, emphasis being placed instead on demonstrating inventive principles and concepts.

For purposes of demonstrating the inventive principles and concepts, the systems and methods will be described with reference to approximating complex musculoskeletal dynamics of the right arm and hand of a human being. However, persons of skill in the art will understand, in view of the description provided herein, that the systems and methods described herein can be used to approximate the musculoskeletal dynamics of any anatomical feature.

FIG. 1 is an OpenSim model 1 of a human right arm and hand showing the geometry of muscle paths as straight and curved lines over the skeletal structure for the displayed posture. The model 1, which is defined by the values shown in Tables 1 and 2 below for the limb shown in FIG. 1, is a known model that was previously developed to capture the relationship between muscle lengths and moment arms in all physiological postures. The model 1 contains a plurality of muscles described with a plurality of musculotendon actuators. The values for the corresponding kinematic variables were obtained on a uniform grid with nine points per DOF, resulting in the domain size of $9^d$ data points per muscle, where d is the number of DOFs that a muscle crosses. For example, since the extensor carpi ulnaris muscle spans two DOFs (wrist flexion-extension and pronation-supination), its moment arms and muscle lengths were sampled in $9^2=81$ positions.

TABLE 1

| id | Name | Range, rad | Description |
|---|---|---|---|
| 1 | ra_wr_s_p | −1.5708 1.5708 | wrist pronation/supination motion |
| 2 | ra_wr_e_f | −1.2217 1.2217 | wrist flexion/extension motion |
| 3 | ra_cmc1_f_e | 0 0.8727 | thumb proximal flexion/extension motion |
| 4 | ra_cmc1_ad_ab | 0 0.8727 | thumb proximal abduction/adduction motion |
| 5 | ra_mcp1_f_e | −0.7854 0 | thumb central flexion/extension motion |
| 6 | ra_ip1_f_e | −1.5708 0 | thumb distal flexion/extension motion |
| 7 | ra_mcp2_e_f | 0 1.5708 | index proximal flexion/extension motion |
| 8 | ra_pip2_e_f | 0 2.0944 | index central flexion/extension motion |
| 9 | ra_dip2_e_f | 0 1.5708 | index distal flexion/extension motion |
| 10 | ra_mcp3_e_f | 0 1.5708 | middle proximal flexion/extension motion |
| 11 | ra_pip3_e_f | 0 2.0944 | middle central flexion/extension motion |
| 12 | ra_dip3_e_f | 0 1.5708 | middle distal flexion/extension motion |
| 13 | ra_mcp4_e_f | 0 1.5708 | ring proximal flexion/extension motion |
| 14 | ra_pip4_e_f | 0 2.0944 | ring central flexion/extension motion |
| 15 | ra_dip4_e_f | 0 1.5708 | ring distal flexion/extension motion |
| 16 | ra_mcp5_e_f | 0 1.5708 | pinky proximal flexion/extension motion |
| 17 | ra_pip5_e_f | 0 2.0944 | pinky central flexion/extension motion |
| 18 | ra_dip5_e_f | 0 1.5708 | pinky distal flexion/extension motion |
| 19 | ra_el_e_f | 0 2.2689 | elbow flexion/extension motion |

The list of simulated DOFs. The last two suffixes separated by underscores indicate the direction of the motion, e.g., "s_p" indicates the motion from supinated to pronated posture.

TABLE 2

| id | Name | Full name | DOFs |
|---|---|---|---|
| 1 | BIC_LO | Biceps brachii long head | 19 1 |
| 2 | BIC_SH | Biceps brachii short head | 19 1 |
| 3 | BRR | Brachioradialis | 19 1 |
| 4 | SUP | Supinator | 1 |
| 5 | PT | Pronator teres | 1 |
| 6 | PQ | Pronator quadratus | 1 |
| 7 | ECR_LO | Extensor carpi radialis longus | 1 2 |
| 8 | ECR_BR | Extensor carpi radialis brevis | 1 2 |
| 9 | ECU | Extensor carpi ulnaris | 1 2 |
| 10 | FCR | Flexor carpi radialis | 1 2 |
| 11 | FCU | Flexor carpi ulnaris | 1 2 |
| 12 | PL | Palmaris longus | 1 2 |
| 13 | FDS5 | Flexor digitorum superficialis (pinky finger) | 2 16 17 |
| 14 | FDS4 | Flexor digitorum superficialis (ring finger) | 2 13 14 |
| 15 | FDS3 | Flexor digitorum superficialis (middle finger) | 2 10 11 |
| 16 | FDS2 | Flexor digitorum superficialis (index finger) | 2 7 8 |
| 17 | FDP5 | Flexor digitorum profundus (pinky finger) | 2 16 17 18 |
| 18 | FDP4 | Flexor digitorum profundus (ring finger) | 2 13 14 15 |
| 19 | FDP3 | Flexor digitorum profundus (middle finger) | 2 10 11 12 |
| 20 | FDP2 | Flexor digitorum profundus (index finger) | 2 7 8 9 |
| 21 | EDM | Extensor digiti minimi | 2 16 17 18 |
| 22 | ED5 | Extensor digitorum (pinky finger) | 2 16 17 18 |
| 23 | ED4 | Extensor digitorum (ring finger) | 2 13 14 15 |
| 24 | ED3 | Extensor digitorum (middle finger) | 2 10 11 12 |
| 25 | ED2 | Extensor digitorum (index finger) | 2 7 8 9 |
| 26 | EIND | Extensor indicis | 2 7 8 9 |
| 27 | EPL | Extensor pollicis longus | 1 2 4 3 5 6 |
| 28 | EPB | Extensor pollicis brevis | 2 4 3 5 |
| 29 | FPB | Flexor pollicis brevis | 4 3 5 |

TABLE 2-continued

| id | Name | Full name | DOFs |
|---|---|---|---|
| 30 | FPL | Flexor pollicis longus | 2 4 3 5 6 |
| 31 | APL | Abductor pollicis longus | 1 2 4 3 |
| 32 | OP | Opponens pollicis | 4 3 |
| 33 | APB | Abductor pollicis brevis | 4 3 5 |
| 34 | ADPT | Adductor pollicis transversus | 4 3 5 |

The list of simulated muscles. The list of DOFs that each muscle spans is shown with the list of id values from the previous table.

To compare quality for the approximations with different known methods that are described below, a dataset (total 1,023,474 points) was used that combined the points used for the creation of the models (675,162, grid of 9 points per DOF per muscle), and an additional test dataset between the fitting data (348,312, grid of 8 points per DOF per muscle).

The aforementioned preselected polynomials that approximate the muscle moment arms and lengths have the polynomial structure given by Equation 1:

$$f(x) = a + \Sigma_p{}^\rho \Sigma_{i_1 \leq i_2 \leq \ldots \leq i_p}{}^d M_{i_1, i_2, \ldots, i_p} \Pi_p{}^p x_{i_j}$$

Equation 1 where a is an intercept, $\rho$ is the user-selected maximum of polynomial power, d is the number of DOFs, $x = (x_1, \ldots, x_d)^T$ is the state vector for each DOF, M is the multidimensional matrix of polynomial terms, and indices in sums and product start at 1. The non-zero values of M and the intercept define the polynomial structure. For example, extensor carpi ulnaris moment arms are described by (a, $M_0$, $M_1$, $M_{00}$, $M_{01}$, $M_{11}$, $M_{000}$, $M_{001}$, $M_{011}$, $M_{111}$) around elbow flexion-extension, and (a, $M_0$, $M_{00}$, $M_{01}$, $M_{11}$, $M_{000}$, $M_{001}$, $M_{011}$, $M_{111}$) around wrist pronation-supination, where index 0 is pronation-supination and 1 is flexion-extension. Values for these non-zero elements were obtained using a known linear pseudoinverse, such as, for example, the Moore-Penrose inverse. As will be described below in more detail, in accordance with a preferred embodiment, terms are added to the polynomial structure given by Equation 1 as needed to improve the approximation, but in a way that greatly reduces the amount of time and resources required to perform the approximation computations.

Figures 2A, 2B:
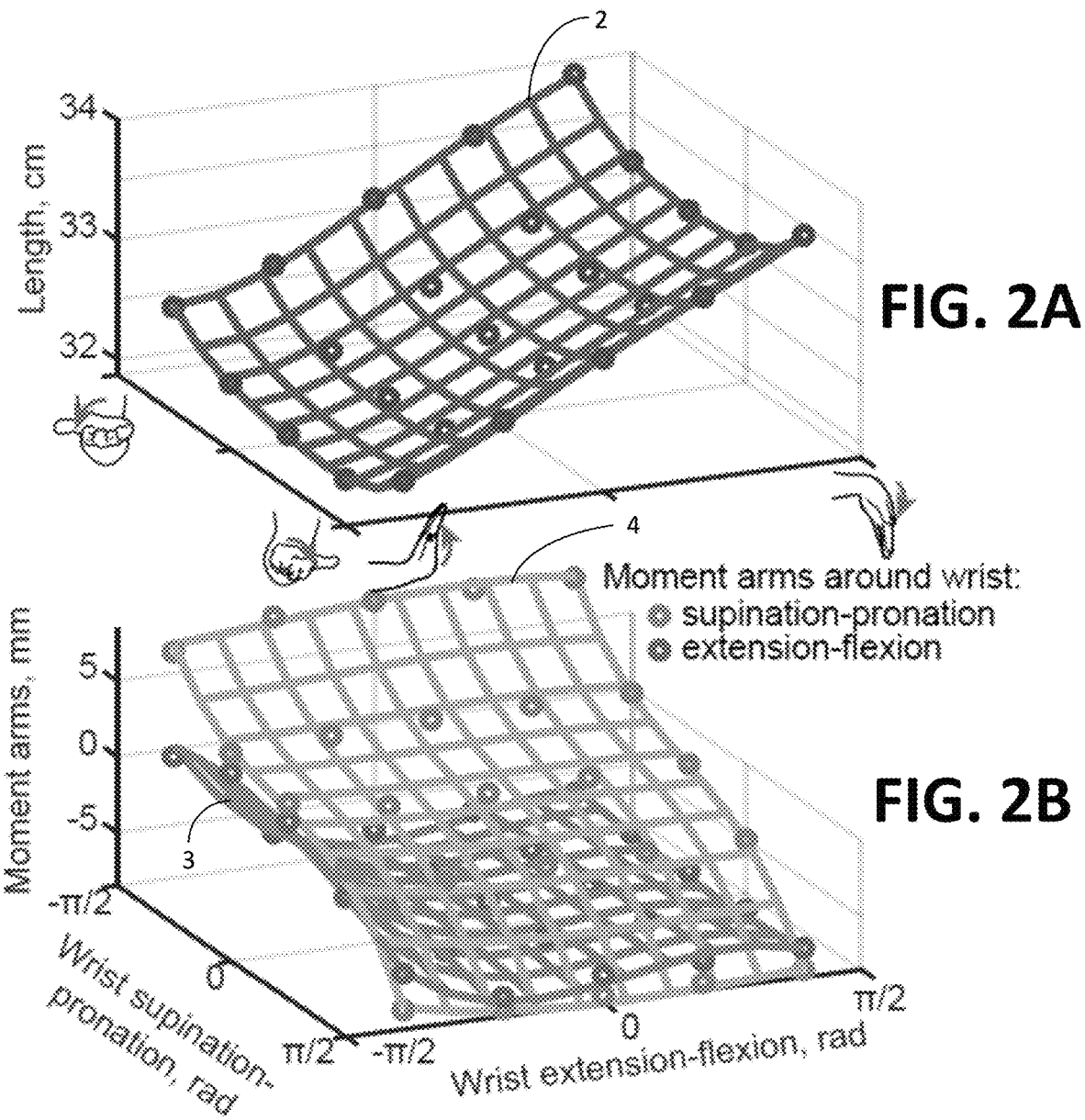
FIGS. 2A and 2B are plots of kinematic variables in terms of muscle length versus (vs.) radians and moment arm vs. radians, respectively, for the extensor carpi ulnaris muscle in different positions of wrist extension-flexion (e-f) and supination-pronation (s-p) degrees of freedom (DOFs).

FIGS. 2A and 2B contain plots 2-4 of kinematic variables in terms of muscle length versus (vs.) radians and moment arm vs. radians, respectively, for the extensor carpi ulnaris muscle in different positions of wrist extension-flexion (e-f) and supination-pronation (s-p) DOFs. The points in FIGS. 2A and 2B correspond to the approximated data. The accuracy of polynomial fit generally increases as the number of terms in the polynomial structure increases. A list of polynomials that contain one more term than a preselected polynomial P(x) will be referred to herein as the list of potential candidates $\Psi(P(x))$ for expansion of the preselected polynomial. Each element of this list is a polynomial with the structure of P(x), but having one additional term that is present in the full polynomial of the correct power and dimensionality, but lacking in P(x). The number of elements in the list equals the number of elements that are present in the full polynomial but lacking in P(x). For example, let P(x) be a two-dimensional polynomial with structure (a, $M_0$, $M_{00}$), full two-dimensional (2-D) polynomial of power 2 has a structure (a, $M_0$, $M_1$, $M_{00}$, $M_{01}$, $M_{11}$). Then the list of potential candidates is: $\Psi(P(x)) = [(a, M_0, M_1, M_{00}); (a, M_0, M_{00}, M_{01}); (a, M_0, M_{00}, M_{11})]$.

Figure 3:
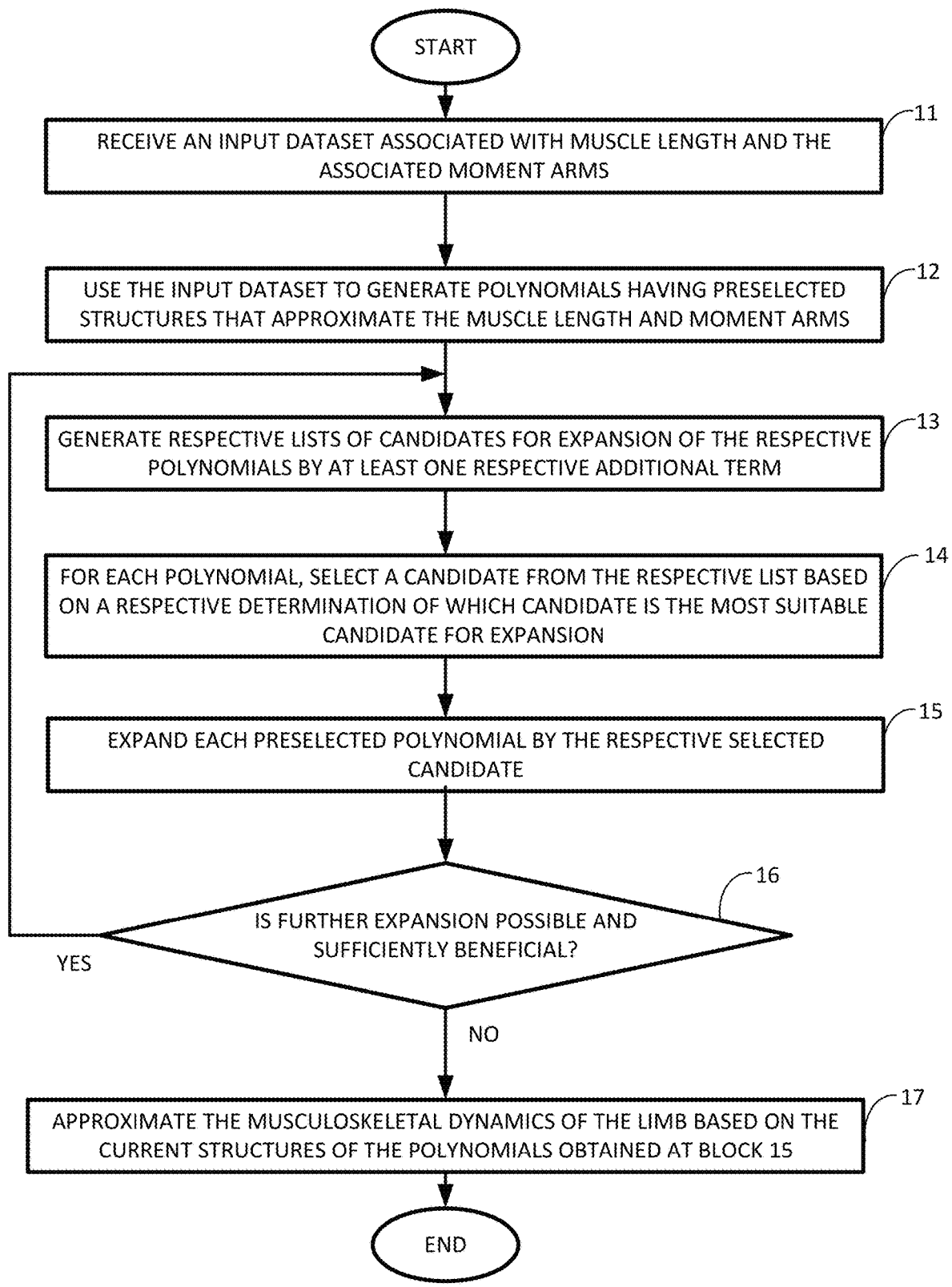
FIG. 3 is a flow diagram representing the approximation method performed by a processor in accordance with a representative embodiment.

FIG. 3 is a flow diagram representing the approximation method performed by a processor or controller in accordance with a representative embodiment. For ease of discussion, the approximation method represented by the flow diagram will be described with reference to polynomials associated with a muscle length and the moment arms of a single muscle for a plurality of limb postures. For this example, it will be assumed that there are two moment arms associated with the muscle. In other words, for this example, the muscle crosses two DOFs. Therefore, the method will use a first polynomial associated with the muscle length and first and second polynomials associated with first and second moment arms, respectively. It should be understood, however, that for a given limb being modeled, the method represented by the flow diagram may be performed for one or more muscles of the limb, for one or more limb postures, for one or more muscle lengths and for the associated moment arms, depending on the application. For example, it may not be necessary to perform the method for all muscles of the right arm and the associated muscle lengths and moment arms if the model is being used to control a right hand prosthetic. The range of simulation can be represented by a single posture or by the full range of postures.

With reference to FIG. 3, an input dataset associated with the muscle length and the two moment arms is received in the processor, as indicated by block 11. The input dataset is used to generate a first polynomial having a preselected structure that approximates the muscle length and first and second polynomials associated with the corresponding moment arms, as indicated by block 12. The preselected structure is an empty list in the beginning, and a polynomial starts without any terms. For each of the polynomials, a list of one or more candidates for expanding the polynomial structure by at least one additional term is generated, as indicated by block 13. For each of the polynomials, one of the candidates on the respective list is selected for expanding the respective polynomial structure based on a respective determination of which of the candidates on the respective list is the most suitable candidate, as indicated by block 14. Each polynomial structure is then expanded by the respective selected candidate, as indicated by block 15. For each expanded polynomial, a determination is made as to whether further expansion of the polynomial structure is possible, and if so, whether expansion would be sufficiently beneficial to warrant expansion, as indicated by block 16. If so, the process returns to block 13. If not, the musculoskeletal dynamics of the limb are estimated based on the current structures of the polynomials obtained at block 15, as indicated by block 17.

In accordance with a preferred embodiment, the approximation method is constrained by a known relationship that exists between muscle length and the associated moment arms, which is given below by Equation 2. Moment arms can be estimated as a partial differential of the associated muscle length in local coordinates as:

$$M_i(x) = \frac{\delta L(x)}{\delta x_i}$$

Equation 2 where i is the index of a DOF actuated by the muscle, $x_i$ is the coordinate of DOF i, $M_i(x)$ is the posture-dependent function of the muscle's moment arm around DOF i, L(x) is the function of muscle length. In accordance with a preferred embodiment, the relationship expressed by Equation 2 is used to constrain the polynomial terms used in the approximation functions for the kinematic variables ($P_L(x)$, $\{P_{Mi}(x)\}$), as will now be described with reference to FIG. 4.

Figure 4:
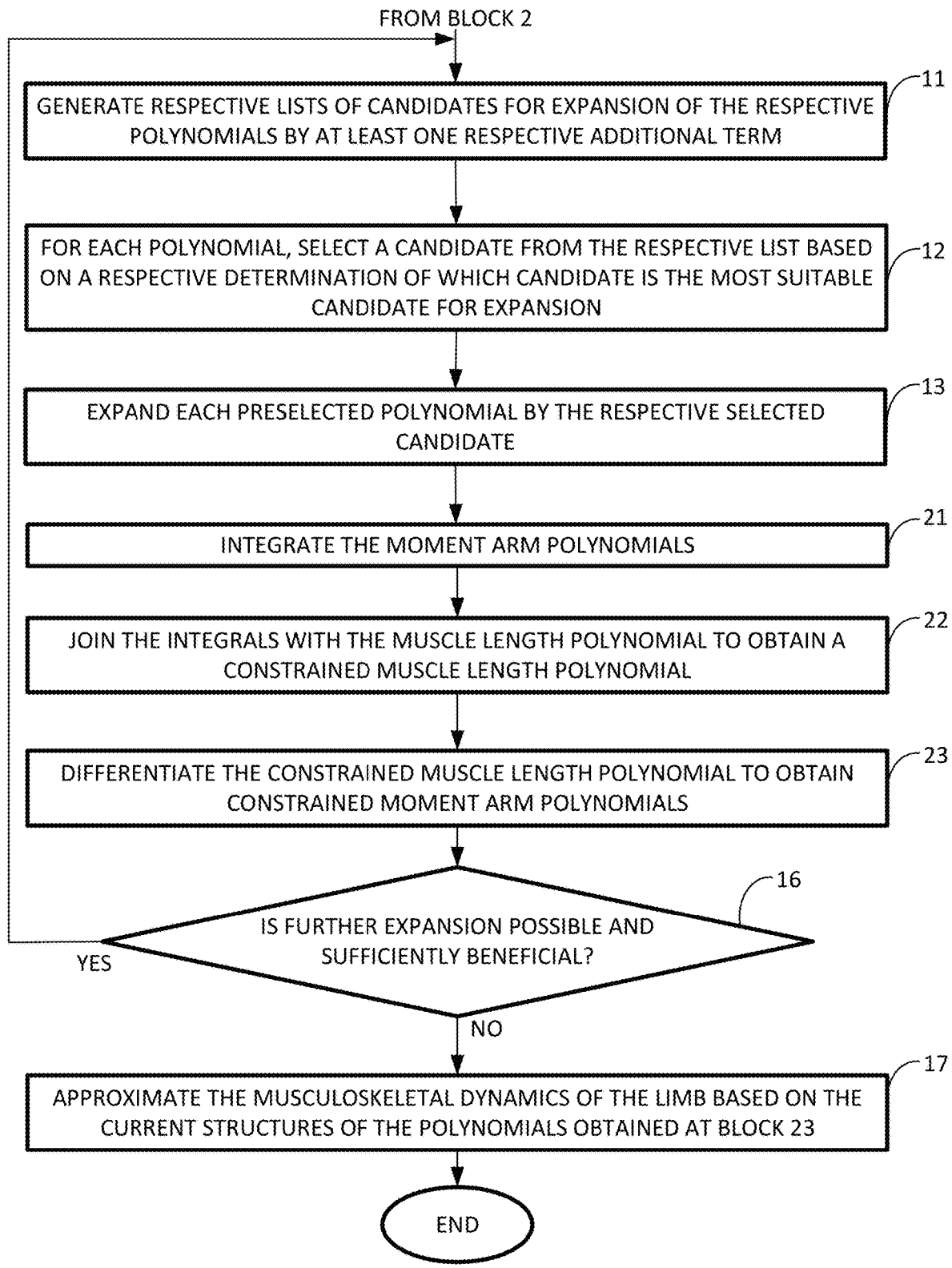
FIG. 4 is a flow diagram representing the approximation method in accordance with a preferred embodiment in which the muscle length polynomial and the moment arm polynomials are constrained by a relationship that exists between muscle length and associated moment arms.

FIG. 4 is a flow diagram representing the approximation method in accordance with the preferred embodiment in which the muscle length polynomial and the moment arm polynomials are constrained by the relationship expressed by Eq. 2. The approximation method is identical to the approximation method represented by the flow diagram shown in FIG. 3 except that additional steps represented by blocks 21-23 in FIG. 4 are performed to constrain the polynomials in accordance with the relationship expressed by Eq. 2. As will be described below in more detail, constraining the polynomials allows the polynomial structures to be optimized, or at least improved, at very high speed, which greatly reduces the overall amount of time that is required to perform the computations.

With reference to FIG. 4, after each polynomial structure has been expanded by the respective selected candidate at the step represented by block 15, the moment arm polynomials are integrated, as indicated by block 21. This process can be expressed as: calculate $\{P_{Li} = \int P_{Mi} dx_i\}$. The integrals are then joined with the expanded muscle length polynomial, as indicated by block 22. This process can be expressed as: $P_L$ or $P_{Li}$: $L = P_L \cup (\cup_i P_{Li})$. The step of joining the integrals with the expanded muscle length polynomial results in a new muscle length polynomial having each term that is present in the integrals and in the expanded muscle length polynomial and having coefficients for the terms that are recalculated using the input dataset obtained at block 11 that the approximation method is attempting to fit. The new muscle length polynomial, $L(x)$, obtained at the step represented by block 22 is then differentiated at the step represented by block 23 to produce new moment arm polynomials, $M_i(x)$. This process can be expressed as:

$$\left\{M_i(x) = \frac{dL(x)}{dx_i}\right\}.$$

For example, let $x=(x_1, x_2)$, $P_L=2x_1x_2^2$, $P_{M1}=3x_1^3+2$, $P_{M2}=5x_1x_2$. Then $P_{L1}=x_1^4+2x_1+$const, $P_{L2}=2.5x_1x_2^2$ const. And the resulting polynomial functions adhering to Eq. 2 are: $L=C_0+C_1x_1x_2^2+C_2x_1^4+C_3x_1$, $M_1=C_4x_2^2+C_5x_1^3+C_6$, $M_2=C_7x_1x_2$, where coefficients $C_{0-7}$ are calculated using the original dataset and a linear pseudoinverse. Similarly, it can be easily described using structures: $P_L$: ($M_{122}$), $P_{M1}$: (a, $M_{111}$) $P_{M2}$: ($M_{12}$); therefore $P_{L1}$: (a, $M_1$, $M_{1111}$), $P_{M2}$: (a, $M_{122}$); and so L: (a, $M_1$, $M_{122}$, $M_{1111}$), $M_1$: (a, $M_{22}$, $M_{111}$), $M_2$: ($M_{12}$).

The process then continues to the step represented by block 16 described above with reference to FIG. 3. Muscle paths vary greatly in their complexity, from the simplest, which barely change with posture and can be approximated with a constant, to very complex that require many polynomial terms. To choose the best polynomial structure, one ought to test each one and choose the best. The number of possible structures representing a muscle across physiological postures grows exponentially with the number of DOFs that a muscle crosses. In accordance with a preferred embodiment, the steps represented by blocks 14-16 comprise an optimization algorithm that is based on forward stepwise regression and that gradually expands the polynomial structures by adding more terms as long as a determination is made at block 16 that the information tradeoff is beneficial, and it is possible to expand the polynomial structures. The information tradeoff is expressed as the corrected Akaike Information Criterion (AICc, Equation 3), which is a correction of Akaike Information Criterion for a finite sample size to avoid overfitting. The lower new value of AICc corresponds to the beneficial choice where a new polynomial approximates the data with higher precision using less variables, higher precision and using the same number of variables, the same precision using less variables, and in some other more complex cases. In accordance with this embodiment, the optimization algorithm compares the models corresponding to the polynomials of the listed expanded potential candidates to one another and chooses the best (the one with the lowest AICc). That model, it turn, is compared to the model created in the previous iteration.

$$AICc(f) = AIC(f) + \frac{2k(k+1)}{N-k-1} = 2k - 2\ln(L) + \frac{2k(k+1)}{N-k-1} \quad \text{Equation 3}$$

where f is the approximation function, AIC is the Akaike Information Criterion, k is the number of parameters in the model, N is the number of data points, and L is the maximum likelihood of the polynomial representing this dataset.

For demonstrative purposes, the AIC calculation assumes a normal distribution of residuals and is based on normalized root means squared $$\left(RMS = \left(\frac{RSS}{N}\right)^{0.5}\right): AICc(f) = \quad \text{Equation 4}$$

$$2k + 2N \ln(RMS) + \frac{2k(k+1)}{N-k-1}$$

The kinematic variables are normalized to preserve consistency in term N·ln(RMS) across DOFs. Muscle lengths are normalized to the range of motion, and moment arms are normalized to the maximum magnitude across postures. If all functions cannot expand anymore (length of $\Psi(F)$ is zero) or if the AICc did not improve in the current iteration, the approximation performs the step represented by block 17 and finishes.

Figure 5:
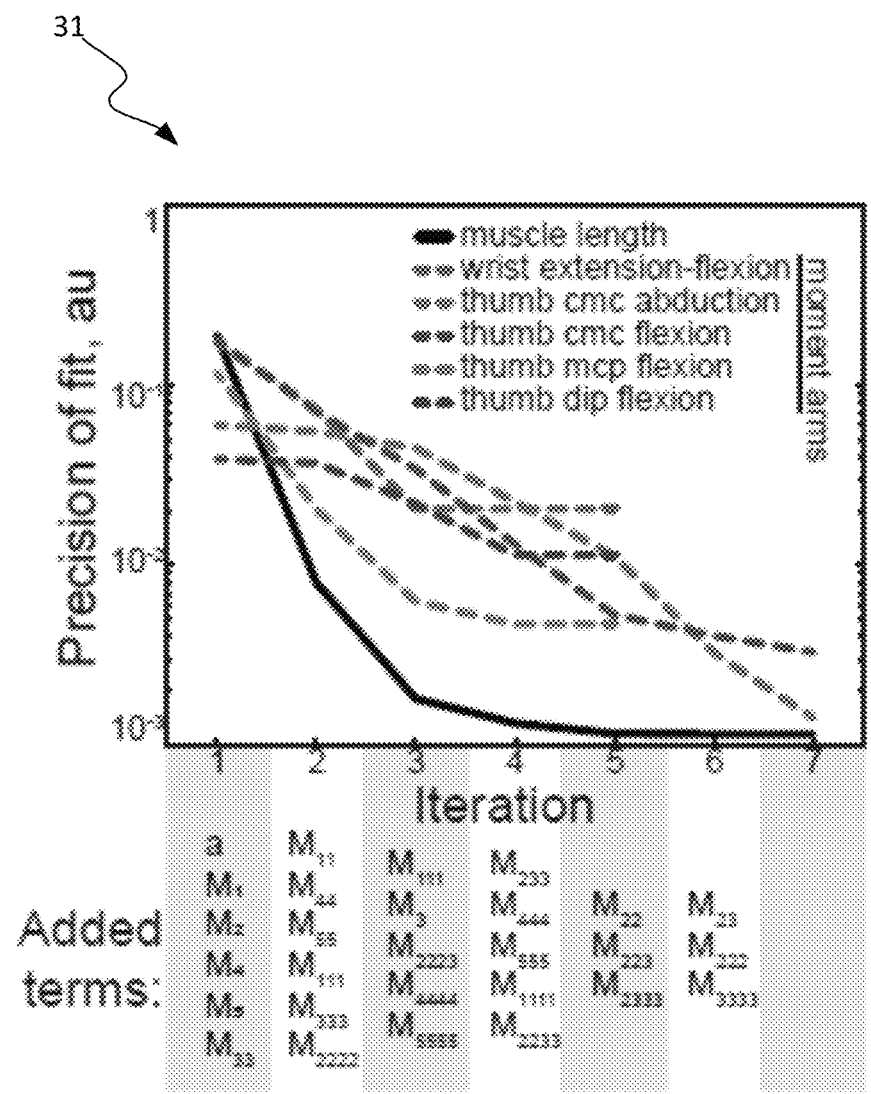
FIG. 5 is a graph showing iteration of the approximation method represented by the flow diagram of FIG. 4 vs. the precision of the fit obtained by the method.

FIG. 5 is a graph 31 showing iteration of the approximation method represented by the flow diagram of FIG. 4 vs. the precision of the fit obtained by the method. The graph 31 shows the progression of the algorithm and optimization of kinematic variables of a single muscle (flexor pollicis longus) and the added terms after each iteration. After the first iteration, the muscle length is approximated by (a, $M_1$, $M_2$, $M_4$, $M_5$, $M_{33}$) an intercept a was added in the step represented by block 15 for $P_L$, other terms came from the step represented by block 21 (from integration of moment arms polynomials). In the second iteration, the approximation expands using elements $M_{11}$, $M_{44}$, $M_{55}$, $M_{111}$, $M_{333}$, $M_{2222}$, and the precision of muscle length fit decreases below 1% (black line). In the fifth iteration, the moment arms around wrist extension-flexion, thumb MCP flexion and thumb DIP flexion have reached the minimum of AICc and were not improved any more. In the seventh iteration, the optimization of remaining kinematic parameters is finished.

The inventors identified how similar the muscles' structures obtained were with adherence to Eq. 2 (flow diagram of FIG. 4) and without adherence to Eq. 2 (flow diagram of FIG. 3). This difference was assessed using a similarity index (SI) that counted common elements in both structures. Structures of polynomials $L_A$ and $L_B$ corresponding to lengths of two muscles, muscles A and B, respectively, can be represented as: $L_A=P_C \cup P_{ANC}$, $L_B=P_C \cup P_{BNC}$, where $P_C$ is the shared structure of terms between $L_A$ and $L_B$; $P_{ANC}$ and $P_{BNC}$ are the non-common polynomial structures of terms present in A and not in B, and vice versa. Then, the similarity index is stated as: Equation 4

$$SI(A, B) = \frac{N_C}{N_{ANC} + N_{BNC} + N_C} \cdot 100\%$$

where $N_C$, $N_{ANC}$, $N_{BNC}$ are the number of terms in $P_C$, $P_{ANC}$, $P_{BNC}$, respectively. SI increases from 0% to 100% when the composition of identical terms increases in two polynomials. The use of Eq. 2 in the search for polynomial terms (flow diagram 4) creates similar polynomials (mean SI>90) and increases the search speed.

The inventors analyzed the similarity of polynomials from different muscles without the bias from the DOFs that each muscle crosses. To do that, the inventors introduced a DOF-independent polynomial vector for each muscle's musculotendon length polynomial. The Agnostic polynomial vector $v=(v_1, \ldots, v_n)^T$ of a polynomial is a nonnegative ($v_i \geq 0$) unit-vector ($\Sigma_i^n v_i^2 = 1$) with length equal to the number of possible term power compositions in a full polynomial of power $\rho=5$ and maximum muscle dimensionality d=6: n=18. Each element of the vector corresponds to a specific power combination in an ordered list. If a power combination on place i is present in a muscle length polynomial, then $v_i$ is equal to the modulus of the M coefficient (Eq. 1), otherwise $v_i=0$. The order of power combinations is: [(1, 1, 1, 1, 1), (1, 1, 1, 1), (1, 1, 1, 2), (1, 1, 1), (1, 1, 2), (1, 1, 3), (1, 1), (1, 2, 2), (1, 2), (1, 3), (1, 4), (1), (2, 2), (2, 3), (2), (3), (4), (5)]. For example, letting $P_L = C_1 x_1 x_2^2 + C_2 x_1^2 x_2 + C_3 x_1^3 + C_4 x_1 + C_5 x_2 + C_6$, then its vector would have $[v_9=|C_1|+|C_2|; v_{12}=|C_4|+|C_5|; v_{16}=|C_3|]$ and all other elements zero. The structural difference of two polynomials was obtained as the Euclidian distance between their vectors. The structural difference is minimal when power composition of all terms and their absolute coefficients are similar in both polynomials even if they cross different DOFs, and large when their power compositions do not have same terms.

The inventors calculated the amount of memory required for spline approximation as a size of MATLAB's '.mat' files that contained single-precision spline parameters saved using '-v7.3' flag, which enables compression. The inventors calculated the amount of memory required for polynomials as the size of executable '.mexw64' files compiled with Visual Studio 2017 C++ with '/O2' optimization. The amount of time required to perform the evaluation was obtained using MATLAB's Profiler. Individual samples for mean and standard deviation of evaluation time were obtained per muscle's dataset during estimation of quality of fit. All computations were performed on a regular personal computer (DELL Precision Workstation T5810 XL with Intel Xeon processor E5-2620 v3 2.4 GHz, 64 GB DDR4 RAM, SK Hynix SH920 512 GB SSD operating under Windows 10).

The composition of approximating polynomials was analyzed with standard statistical tools to test their validity. The root mean square values were used to evaluate errors in the approximated values relative to the dataset used for fitting and the independent testing dataset. The linear regression was used to test the relationship between the complexity of a muscle's physiological function in the form of the number of DOFs it spans and the complexity of the approximating polynomials.

The similarity of composition across multiple muscle groups was tested with the dimensionality reduction analyses, i.e., principle component analysis (PCA) and hierarchical clustering. The Euclidean distance between the muscle vectors in the DOF-independent basis (described above) was first analyzed with the average linkage hierarchical clustering implemented in SciPy. It is a common approach where the distance from a cluster to another cluster is an average distance between elements of these two clusters. Then, the dominant relationship in this distribution of muscle vectors was analyzed with PCA (Scikit-learn module).

The representation of structural and functional information within the polynomial structure was further tested by comparing the distributions of the distances between muscles with similar and different structure or function. The normality of these distributions was tested with D'Agostino's K-squared test that measures deviation from normal skewness and kurtosis. For normal distributions, a one-tailed t-test was used to test if distances between similar (functionally or structurally) muscles was smaller than distances between dissimilar muscles. The non-normal distributions were compared with Mann-Whitney U test (from SciPy module), which calculates the likelihood that a sample from one distribution will be less than a sample from another distribution. This test is nearly as efficient as t-test on normal distributions. Additionally, a simpler one-sample test was performed to compare the differences between elements in the two distributions to zero. A sign test was used to test if the median of that distribution was below zero. The sign test was used instead of the Wilcoxon signed-rank test, because the latter assumes symmetrical distribution of differences around the median.

Results

Approximation of Muscle Lengths and Moment Arms

FIGS. 6A and 6B illustrate histograms 51 and 52 of the normalized error in estimation of muscle lengths and moment arms, respectively, using splines and optimized polynomials with and without the aforementioned constraint associated with steps 21-23 of FIG. 4. For the purposes of error visualization, 1% of outliers (see Table 1) are omitted. In this study, musculoskeletal kinematics of a human hand were precisely (error <3%, see Table 3 below) and efficiently (see Table 4 below) represented as a system of polynomials. FIG. 7A illustrates a graph 55 of similarity index (SI) vs. number of muscles for polynomials defined with the constraint stated as the equality between muscle length partial differentials in local coordinates and its moment arms. It demonstrates that the methods described in FIG. 3 and FIG. 4 produce the muscle length polynomials of similar structure. FIG. 7B illustrates a graph 56 of the number of joints the muscle spans vs. the number of terms in the approximating polynomials, which demonstrates that the number of terms increases with the number of joints the muscle spans. FIG. 7B shows the relationship between the number of terms in the muscle length polynomial (circles) and the number of DOFs each muscle spans (dashed, y=7.3112x−1.5604, r=0.7137, p<3·10$^{-6}$). The right side of FIG. 7B shows the distribution of polynomial complexity expressed as the number of terms.

Figures 8A, 8B:
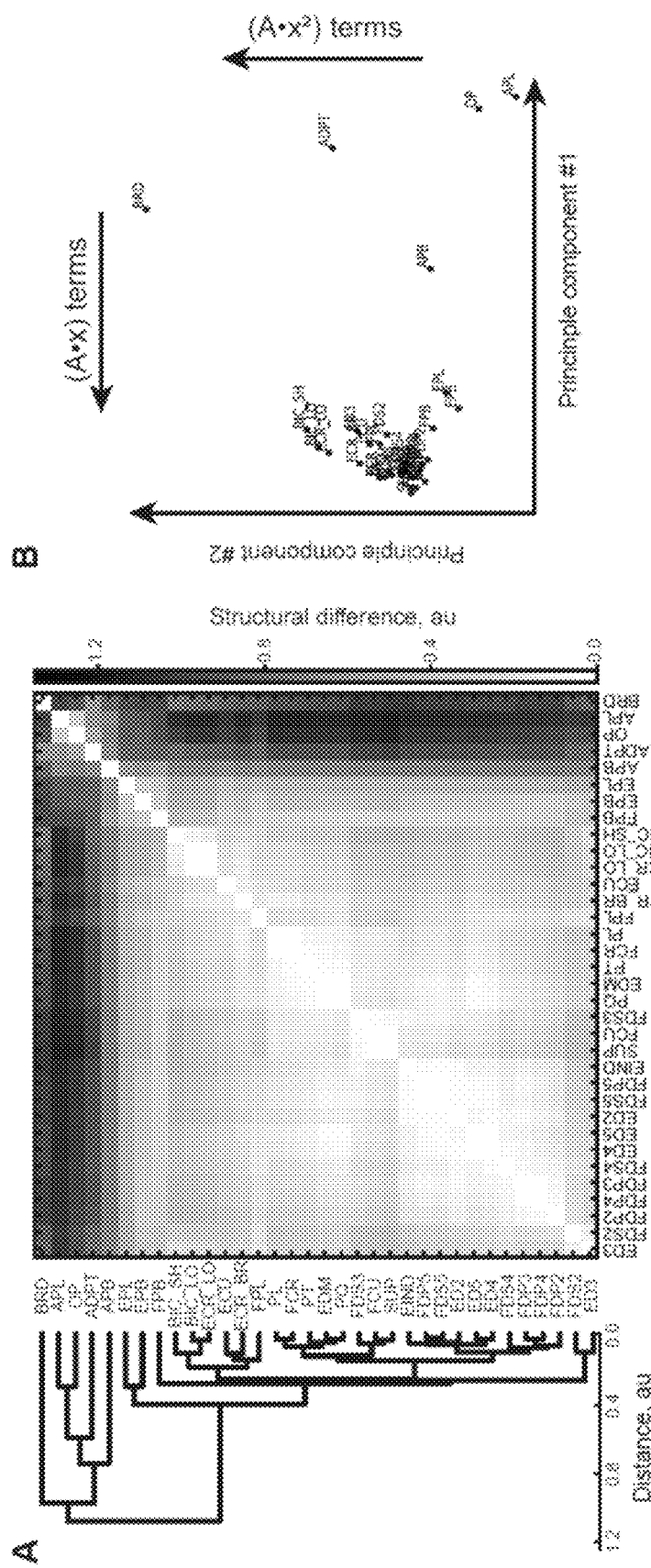
FIG. 8A shows an average-linkage dendrogram and the heatmap of distances between muscle vectors in the space defined by the polynomial terms that are independent of DOF identity.
FIG. 8B shows all muscle vectors in the axes of the two first principle components: x-axis represents linear (x) terms and y-axis represents quadratic ($x^2$) terms.

FIGS. 8A and 8B demonstrate the non-random structure in the composition of polynomials. FIG. 8A shows an average-linkage dendrogram and heatmap of distances between DOF-independent vectors of muscles' lengths. FIG. 8B shows the muscle vectors in the axes of two first principal components corresponding to terms x (horizontal axis) and $x^2$ (vertical axis).

A combination of fitting and testing of the dataset was used to evaluate the precision of the known spline model and the polynomial model in accordance with the inventive principles and concepts. Splines and both types of polynomials (adhering and not adhering to the constraint described by Eq. 2) approximate moment arms with <3% error and muscle length with <0.2% error, as can be seen from FIGS. 6A and 6B and Table 3 below. Although the spline approximation error has a smaller deviation from zero, it is much harder to interpret (see Total number of parameters in Table 3). The AIC was used to assess the relative quality of statistical models to represent the phenomena by calculating the tradeoff between increasing precision and adding more variables. The AIC of the polynomial model of the kinematic variables ($-1.610^7$ and $-10^7$) is significantly smaller than AIC of the spline model ($2.2*10^9$ and $3.2*10^{10}$), which shows better relative quality of the polynomial model. Addition of the partial differential constraint (Eq. 2) did not significantly change the precision of the polynomial model (p>0.95 and Table 3) and AIC. Their error distributions in FIGS. 6A and 6B are not distinguishable.

presence or absence of terms in functions for muscle lengths, calculated with and without adherence to the length-moment arm constraint (Eq. 1) for the same muscle. With reference again to FIG. 5, it shows that both optimizations found very close polynomials (SI≥80%) for a majority of muscles (29). On average, they have a 90% difference, and the maximum difference is about 35%. The differences in structures appear when the constrained polynomials retain the terms adopted from moment arm polynomials.

The number of polynomial terms in the muscle length grows with the number of degrees of freedom that a muscle crosses (FIG. 7B, r=0.71). However, the relative complexity of the polynomial measured in the fraction of parameter space occupied decreases. Interestingly, thumb muscles (ADPT, FPB, APB, EPB, APL, FPL, EPL) stay above the regression line, indicating a higher than average complexity, while finger muscles (FDS2-5, FDP2-5, ED2-5, EDM, EIND) stay below, suggesting a lower relative complexity.

TABLE 3

The comparison of spline and two polynomial approximations with (constrained) and without (unconstrained) the constraint linking muscle lengths and moment arms, as described by algorithm in Model Physical Constraints in Methods. Values are given ± standard deviation and a maximum absolute percent. Approximation methods used: CS—cubic splines, UP—unconstrained polynomials, CP—constrained polynomials.

| Method | Normalized error, % | | Normalized error w/o outliers, % | | Total number of parameters | | AIC, au | |
|---|---|---|---|---|---|---|---|---|
| | L | MA | L | MA | L | MA | L | MA |
| CS | $-1*10^{-4} \pm 1.2*10^{-2}$, 1.23 | $-0.018 \pm 0.27$, 19.46 | $-1*10^{-4} \pm 5.8*10^{-3}$, 0.06 | $-0.018 \pm 0.22$, 1.85 | $1.1*10^9$ | $16.4*10^9$ | $2.2*10^9$ | $3.2*10^{10}$ |
| UP | $-2*10^{-4} \pm 5.2*10^{-2}$, 2.5 | $-0.024 \pm 0.65$, 18.68 | $-1*10^{-4} \pm 3.0*10^{-2}$, 0.14 | $-0.025 \pm 0.54$, 2.52 | 644 | 749 | $-1.6*10^7$ | $-1.0*10^7$ |
| CP | $-2*10^{-4} \pm 5.2*10^{-2}$, 2.4 | $-0.024 \pm 0.65$, 17.77 | $-1*10^{-4} \pm 3.0*10^{-2}$, 0.14 | $-0.025 \pm 0.54$, 2.52 | 700 | 841 | $-1.6*10^7$ | $-1.0*10^7$ |

TABLE 4

Time and memory requirements of approximations methods for kinematic variables.

| Method | Time of evaluation, ms | Time of generation, min | Memory, KB |
|---|---|---|---|
| CS | 128.6633 ± 6.0872 | 33 | 17,800,000 |
| UP | 0.0147 ± 0.0017 | 297 | 139 |
| CP | 0.0161 ± 0.0030 | 114 | 166 |

The distribution of evaluation time for splines and polynomial models was obtained by separating the dataset into 30 muscle-based groups and measuring time spent evaluating the approximation function in each of the groups. Both polynomial models generated with and without Eq. 2 (constrained and unconstrained) are evaluated faster than the spline approximation models (over $10^4$ times faster, Table 4) and require less memory ($10^5$ times smaller). When the relationship between muscle length and moment arm associated with Eq. 2 contributed to the selection of polynomial terms, as described above with reference to FIG. 4, the search time for the best-fit polynomial model decreased by a factor of at least two. This was accomplished without a change in the overall accuracy of fits, as demonstrated by FIGS. 6A and 6B.

Structure of Approximating Polynomials

Both polynomial models are similar in composition. We examined the difference in polynomial structure, i.e., the Structure and Function To investigate the information embedded within the polynomials of all muscles, the inventors developed DOF-independent vectors that represented the relative contribution of terms with specific power composition to the overall profile of muscle length polynomial. These nonnegative unit-vectors belong to a space where each axis corresponds to a power composition of a polynomial term with maximum total power of 5 (e.g. $x_i^2 x_j$ has power composition (2, 1)). Differences between muscles were then measured as Euclidean distances between their vectors. To visualize the resulting 18-dimensional space, the inventors generated a heatmap with a dendrogram (FIG. 8A) and projected these vectors on two first principle components (FIG. 8B).

It can be noted in FIGS. 8A and 8B that thumb muscles (ADPT, APB, OP, APL, and EPL, EPB, and FPB to lesser extent) are visibly separated from all other muscles. At the small relative distances, three clusters on the dendrogram and heatmap are visible. They can be assigned a function based on the majority of muscles within them: finger muscles (FDP2-5, FDS4, FDS5, ED2, ED4, ED5, EIND), wrist flexors and rotators located on the forearm (FCU, FCR, PT, PQ, SUP), biceps brachii and extensors (BIC_SH, BIC_LO, ECR_LO, ECR_BR, ECU). A large portion of the muscle vector variance (88%) is explained by the first two principle components. They have their largest coefficients associated with linear ($k_{12}$=-0.72) and square ($k_{15}$=0.83) power compositions, respectively (index 12 corresponds to axis associated with power combination (1) in the DOF-independent power vector, and 15—(2), see Methods). From that, the group of muscles in the bottom-left corner of FIG. 6B is dominated by linear terms, thumb muscles (bottom and bottom-right) rely on linear terms less than others, and brachioradialis (BRD) uses square term much more than the linear ($v_{12}$=0.18, $v_{15}$=0.95). Overall, the space of the muscle polynomial vectors appears to be not random and suggests internal organization based on muscle anatomy or function.

FIG. 9A is a graph 61 showing distributions 71 and 72 of distances between muscles that share an anatomical DOF (71) and between muscles that do not share a DOF (72). FIG. 9B is a graph 62 showing a probability density distribution 73 of difference in distance between muscles that share a DOF and muscles that do not. FIG. 9C is a graph 63 showing distributions 74 and 75 of distances between muscles that belong to the same functional group and share a DOF (74) and muscles that do not (75) but share a DOF. FIG. 9D is a graph 64 showing a probability density distribution 76 of difference in distance between muscles that belong to the same functional cluster and muscles that do not, while all of them share a DOF. Box plots in FIGS. 9A, 9B, 9C and 9D indicate a median and $25^{th}$-$75^{th}$ quantile region. Asterisks in FIGS. 9A, 9B, 9C and 9D indicate $p<10^{-8}$ in the statistical comparisons with α=0.05.

To determine whether the muscle vectors contain information about their anatomical structure, the inventors performed attest to determine whether muscles crossing the same DOFs will be closer to each other in the vector space than to muscles that do not cross the DOF. To do that, the inventors generated three distributions: distances between muscles that share a DOF (FIG. 9A, bars 71); distances between muscles that do not share a DOF (FIG. 9A, bars 72); difference in distance (FIG. 9B, bars 73). The first distribution (FIG. 9A, bars 71) contains distances between two muscles, both crossing the DOF, for all DOFs. The second distribution (bars 72) contains distances between two muscles, one of which crosses the DOF, and the other of which does not, for all DOFs. In this approach, the distance between two muscles may appear in the first distribution 71 when looking at one DOF, and the second distribution 72 when looking at another DOF. The third distribution (FIG. 9B, bars 73) contains all possible differences in distance between muscles: DD=d(A, B)-d(A, C), where muscles A and B share a DOF, A and C do not, with respect to each DOF. Because of similarity between finger joints (MCP, PIP, DIP) of different fingers in our model and lack of hand-based finger muscles, MCP of fingers 2-5 were treated as equal in this analysis, as were PIP and DIP.

All three distributions 71-73 were not normal (D'Agostino, $p<10^{-8}$). The first two distributions 71 and 72 were significantly different with muscles that have similar anatomical paths being closer to each other (Mann-Whitney U=8·10$^5$, $p<10^{-8}$). The median of the third distribution 73 was less than zero (sign test, $p<10^{-8}$). These results support that DOF-independent muscle vectors contain information on muscle anatomy. FIGS. 9A and 9B demonstrate that the polynomial term composition of the muscle length polynomials captures the anatomical relationship among muscles. FIGS. 9C and 9D demonstrate that the polynomial term composition of the muscle length polynomials captures the functional relationship among muscles.

To determine whether the muscle vectors contain information about their physiological function, not explained by the anatomical similarities, the inventors performed tests to determine whether muscles that share a DOF, but have different functions, will be farther apart than muscles that share a DOF and have similar function. Again, three distributions 74-76 were generated: distances between muscles that share a DOF and are within the same functional group (FIG. 9C, bars 74); distances between the muscles that share a DOF but belong to different functional groups (FIG. 9C, bars 75); difference in distance (FIG. 9D, bars 76). All modelled muscles were separated into seven functional groups: wrist supinators (BIC_LO, BIC_SH, BRD, SUP), pronators (PT, PQ), extensors (ECR_LO, ECR_BR, ECU), flexors (FCR, FCU, PL), finger flexors (FDS2-5, FDP2-5), extensors (ED2-5, EDM, EIND), and thumb muscles (APL, OP, APB, EPL, EPB, FPB, FPL, ADPT). Each muscle was assigned to a group based on its primary function in the hand and forearm.

All three distributions 74-76 were again not normal (D'Agostino, $p<10^{-8}$). The distributions 74 and 75 were significantly different with muscles that have similar function being closer to each other (Mann-Whitney U=5·10$^6$, $p<10^{-8}$). The median of the third distribution 76 was less than zero (sign test, $p<10^{-8}$). These results support the conclusion that DOF-independent muscle vectors contain information on muscle function not explained by the muscle anatomy.

Although both tests showed significance, the median in FIG. 9B is almost twice as far from zero as the median in FIG. 9D (−0.13 and −0.07, respectively). In summary, these results support the idea that the polynomial term composition of muscle lengths is not random and reflects muscle anatomy and function.

Figure 10:
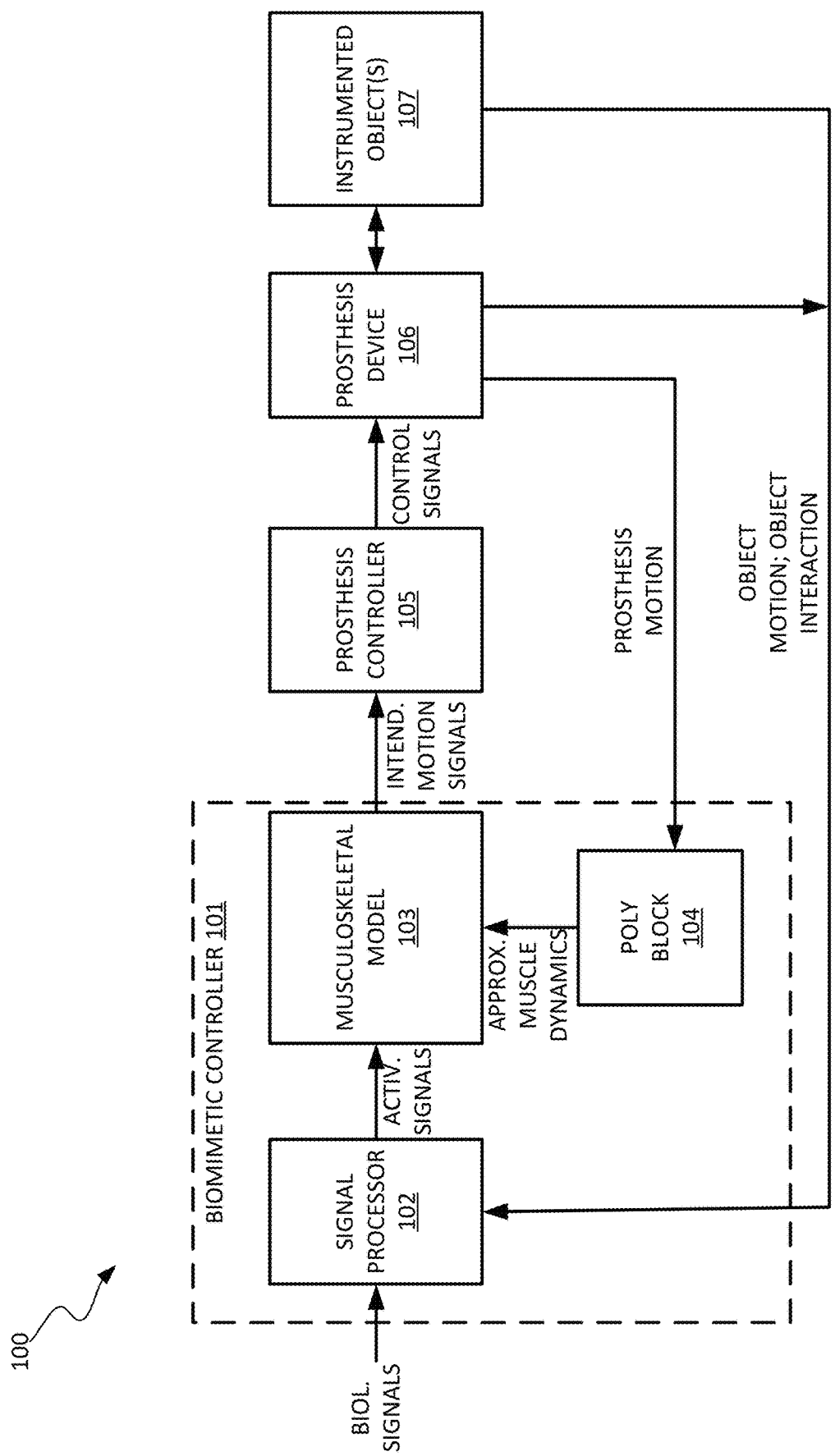
FIG. 10 is a block diagram of a system in accordance with a representative embodiment that enables biomimetic processing of biological inputs in order to control an actual prosthesis device.

FIG. 10 is a block diagram showing the system 100 in accordance with a representative embodiment that enables biomimetic processing of biological inputs in order to generate control signals for controlling a myoelectric prosthetic device in real-time. A biomimetic controller 101 of the system comprises a signal processor 102, musculoskeletal model 103 and a polynomial (Poly) block 104. The signal processor 102 receives M biological signals from a subject, where M is a positive integer that is greater than or equal to 1, and expands the M biological signals into N activation signals, where N is a positive integer that is greater than M. The activation signals are outputted from the signal processor 102 and are inputted to the musculoskeletal model 103. The musculoskeletal model 103 converts the activation signals into intended motion signals, which are outputted from the musculoskeletal model 103 and inputted to a prosthesis controller 105 of the system 100.

The prosthesis controller 105 converts the intended motion signals into control signals, which are outputted from the prosthesis controller 105 and inputted to a prosthesis device 106 that is worn by a subject, or patient (not shown). The prosthesis device 106 performs one or more tasks in accordance with the control signals received from the prosthesis controller 105.

In accordance with an embodiment, the prosthesis device 106 comprises one or more sensors that detect motion of the prosthesis device 106 as it performs one or more tasks in accordance with the control signals received from the prosthesis controller 105. The output of the sensor(s) is fed back to the Poly block 104. The Poly block 104 uses this feedback in approximating the muscle dynamics in accordance with the approximation method of the parent application described above with reference to FIGS. 1-9B. As indicated above, the polynomial structures of the Poly block 104 preferably are determined a priori to allow the system 100 to operate in real-time. The computation-intensive simulation of musculotendon kinematics is replaced by accurate and optimal approximations of this process. The approximated muscle dynamics are inputted to the musculoskeletal model 103, which uses them in generating the intended motion signals that are delivered to the prosthesis controller 105. This allows the prosthesis controller 105 to modify, if necessary, the control signals that are delivered to the prosthesis device 106 to better control the tasks that are being performed by the prosthesis device.

In accordance with another embodiment, the system 100 includes one or more instrumented objects 107 that the prosthesis device 106 interacts with while performing tasks. The instrumented object(s) 107 output feedback signals that reflect the motion of the instrumented object(s) and/or interaction (e.g., gripping, picking up) between the prosthesis device 105 and the instrumented object(s) 107. These feedback signals may be used by the signal processor 101 to expand the M biological signals into the N activation signals.

Figure 11:
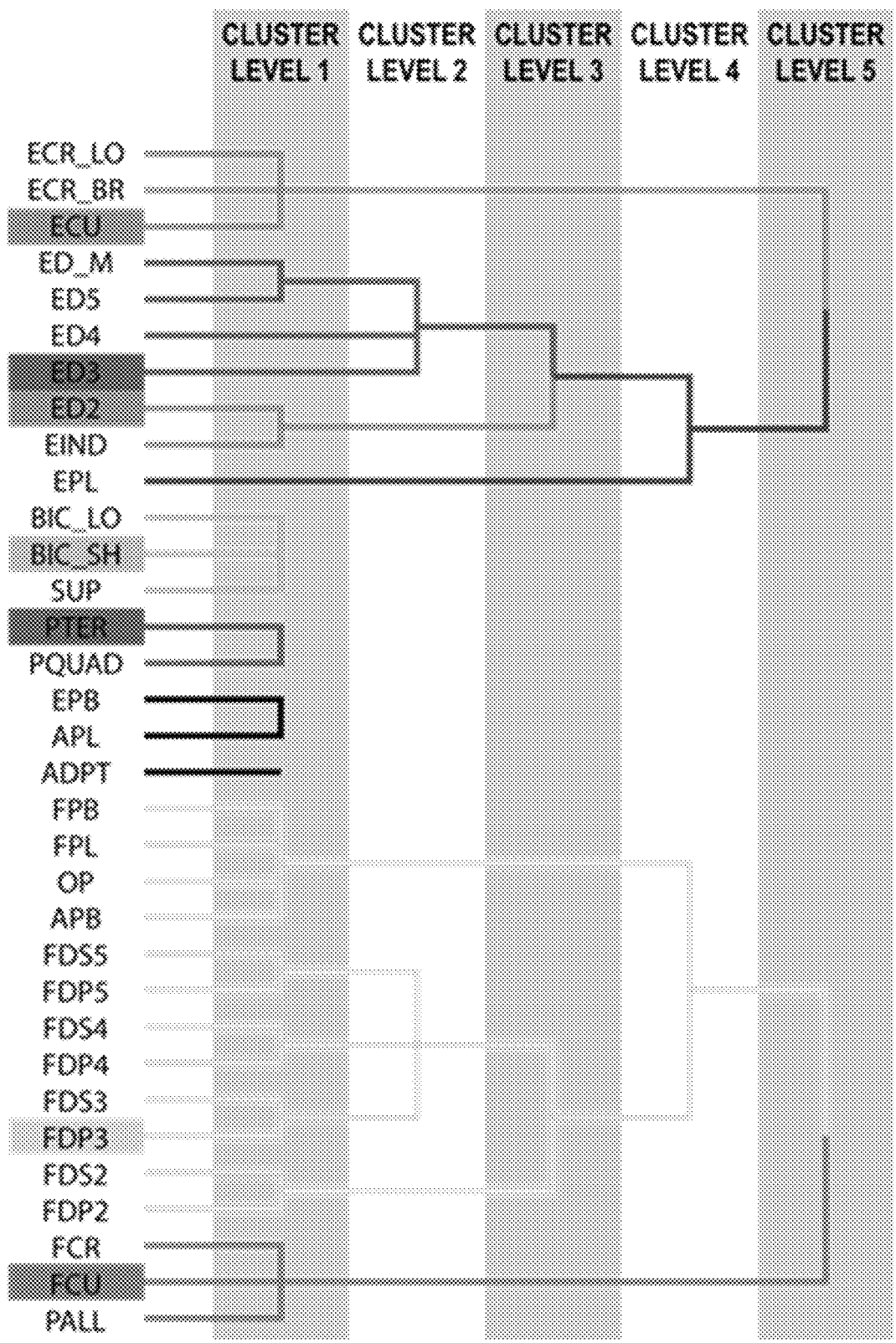
FIG. 11 illustrates a dendrogram that shows the transformations inside the signal processor shown in FIG. 10 and lists acronyms corresponding to a set of N simulated activation signals that are generated from a subset of M available biological signals based on the illustrated dendrogram.

Biological signals can be grouped into agonists and antagonists based on their anatomy. This relationship can be represented mathematically to expand sparse biological signals into higher-dimensional activation signals. The activation signals produce movements through mechanical coupling, which defines the space of independent DOFs that are possible given the particular set of sparse biological signals. FIG. 11 illustrates a dendrogram that shows the association of sparse input signals with the full set of simulated signals inside the signal processor 102 and lists acronyms corresponding to a set of N simulated activation signals that are generated from a subset of M available biological signals based on the illustrated dendrogram. For example, if only four (M=4) biological signals from wrist and finger muscles are available (e.g., FCU, ECU, FDS2, and ED3), then activation signals will be produced at the cluster level 5. Each biological signal is copied to other members of its cluster and scaled with a coefficient that is proportional to the anatomical relationship between each activation signal and the source biological signal.

Thus, in the system 100, the number of available biological signals is smaller than the number of activation signals and is smaller than the number of DOFs that are controlled by the prosthesis controller 105. In accordance with a representative embodiment, the system 100 is capable of simultaneously controlling at least three DOFs, and typically at least four DOFs, with a loop time that can be less than 2 milliseconds (ms), which is not believed to have been possible until the present invention. The loop time is defined as the time between the moment of sending a packet of biological signals to the system 100 and the moment of a set of output control signals from the controller 105, at which point the system is ready to process the next packet of biological signals.

Although it will be understood that the inventive principles and concepts presented herein are not limited to any particular anatomical feature, examples of DOFs, as that term is used herein, include:

1 DOF is flexion/extension of 2nd-5th metacarpophalangeal joints driven by a single control signal (all fingers 2-5 move together);

1 DOF is flexion/extension of 1st carpometacarpal joint of the thumb driven by a single control signal (independent control of the thumb);

1 DOF is abduction/adduction of 1st carpometacarpal joint of the thumb driven by a single control signal (independent control of the thumb); and 1 DOF is flexion/extension of wrist joint driven by a single control signal (independent control of the wrist).

Figure 12:
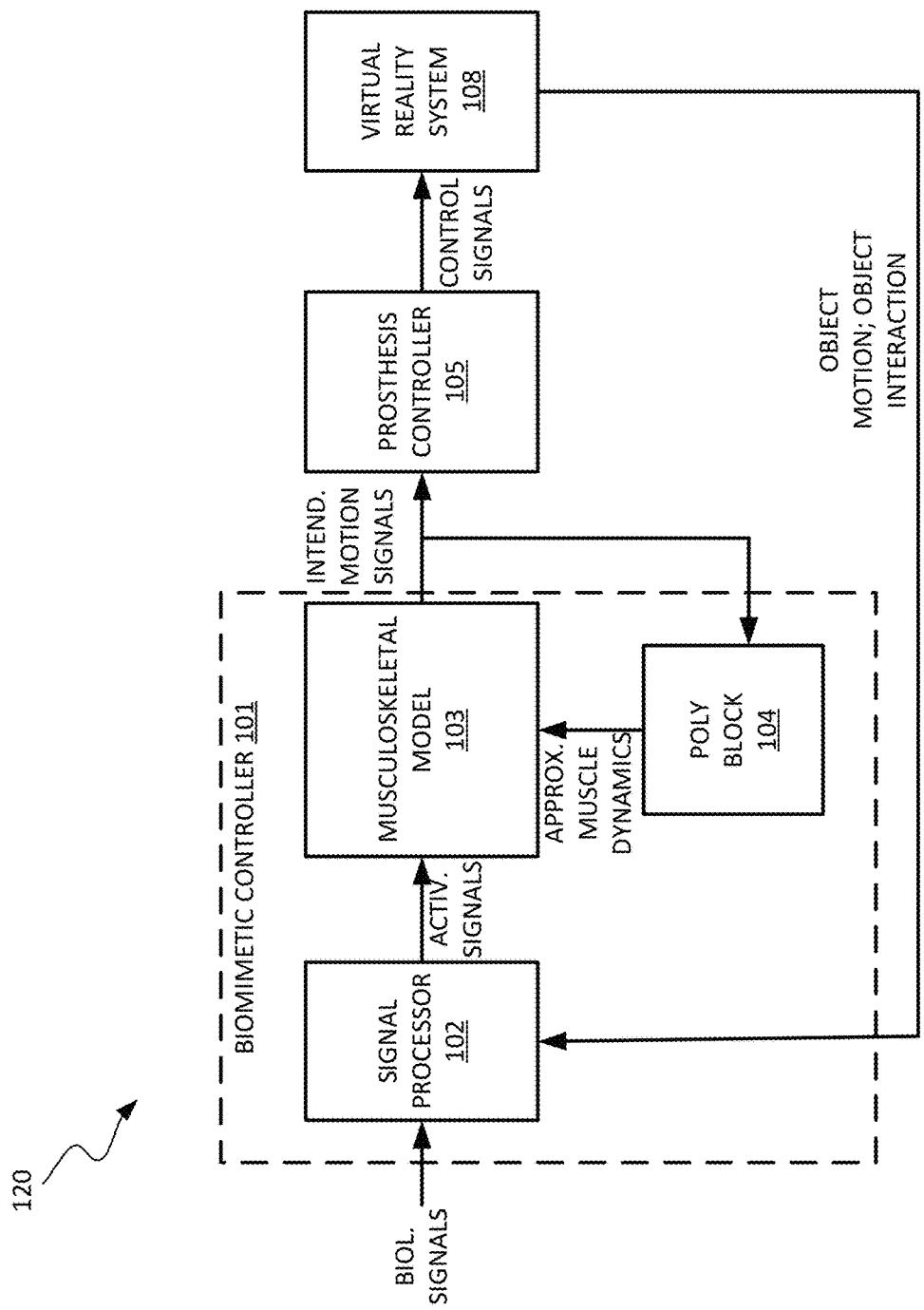
FIG. 12 is a block diagram showing the system in accordance with a representative embodiment that enables biomimetic processing of biological inputs in order to generate control signals for controlling a virtual reality (VR) prosthesis system.

FIG. 12 is a block diagram showing the system 120 in accordance with a representative embodiment that enables biomimetic processing of biological inputs in order to generate control signals for controlling a virtual reality (VR) prosthesis system. The signal processor 102 receives M biological signals from a subject, where M is a positive integer that is greater than or equal to 1, and expands the M biological signals into N activation signals, where N is a positive integer that is greater than M. The activation signals are outputted from the signal processor 102 and are inputted to the musculoskeletal model 103. The musculoskeletal model 103 converts the activation signals into intended motion signals, which are outputted from the musculoskeletal model 103 and inputted to the prosthesis controller 105 of the system 120.

The prosthesis controller 105 converts the intended motion signals into control signals, which are outputted from the prosthesis controller 105 and inputted to the VR prosthesis system 108 that is worn by a subject or patient (not shown). The VR prosthesis system 108 moves the avatar of the prosthesis or the user's hand in accordance with the control signals received from the prosthesis controller 105. Direct control of four or more DOFs of the avatar can mean, but is not limited to, virtual gripper opening and closing with simultaneous flexion or extension and rotation of the wrist and flexion or extension or the elbow.

In accordance with this embodiment, the VR prosthesis system 108 measures virtual motions it performs or virtual interactions it performs with one or more objects in accordance with the control signals received from the prosthesis controller 105 and outputs feedback signals that reflect the virtual motions and/or virtual interactions. These feedback signals may be used by the signal processor 101 when it performs the algorithm described above that expands the M biological signals into the N activation signals.

In addition, the intended motion signals are fed back to the Poly block 104 and processed by the Poly block 104 to approximate the muscle dynamics that are delivered to the musculoskeletal model 103. The musculoskeletal model 103 processes the activation signals and the approximated muscle dynamics to generate the intended motion signals, which are then processed by the prosthesis controller 105 to generate the control signals that are delivered to the VR system 108.

The feedback signals and the manner in which they are processed in the system 120 allow the control signals that are delivered to the VR system 108 to be varied to achieve more precise control of the VR system 108. This, in turn, allows the VR system 108 to be used for training.

Despite technological advances in prosthetic design, myoelectric prostheses can be difficult to control. The forethought required to operate this type of device in a complex way can be quite burdensome. This can lead to passive-use of the device, which can have detrimental effects on the contralateral limb due to overuse. Moreover, several studies suggest an increased rate of rejection of myoelectric prostheses with lengthened follow-up. Providing extensive training as well as intuitive and robust control for myoelectric prostheses may reduce injuries and increase usability.

In an experimental setup of the system 120 shown in FIG. 12, the VR environment of the VR system 108 includes a dynamic model of a prosthetic hand and simulated its interaction with the external world, providing the user with visual feedback. This type of environment allows the patient to learn how to use a prosthetic device and to select a prosthetic device that is most suitable for the patient. Once a patient is fitted with a prosthetic device, its success is based on its usefulness in everyday life. Thus, the ability to enable a patient to train on the system 120 before selecting and being fitted with a prosthetic limb is very beneficial. In addition, studies have been conducted that show that virtual reality enables the brain to embody a virtual limb and thus help reduce phantom pain. Other studies show that a technique that involves virtual reality and neural stimulation can help change an amputee's phantom limb to more closely match their prosthetic limb, making it easier and more natural to use.

The system 120 can function as a tool to improve fitting, adjustment, and usability of high DOF prostheses. The system 120 can encompass all phases of interactions between health professionals and patients, including preliminary prosthesis selection using virtual reality at home, clinic-based fitting and assessment of patient performance with the prosthesis, and clinic- and home-based rehabilitation. The clinicians can tune the prosthesis controller 105 to the patient's needs and to the level of amputation, which determines the number of available biological signals and, consequently, the number of available functions. Patients would be more involved in the prosthesis selection process through testing and familiarization with multiple devices and controller settings. Through better understanding of the needs and limitations of the user at the beginning of the process, clinicians can more efficiently fit complex prosthetics and provide customized training.

Figure 13:
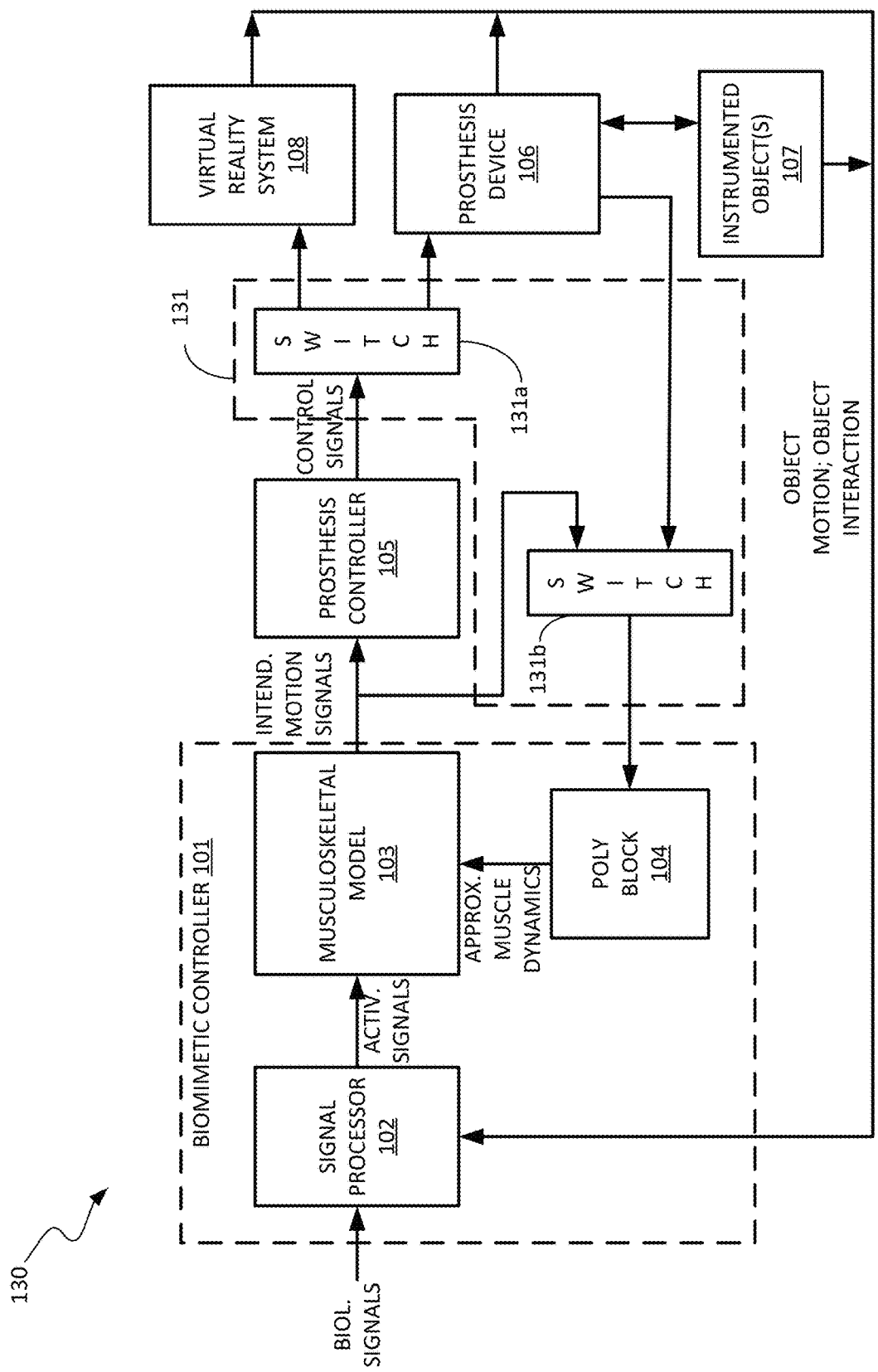
FIG. 13 is a block diagram of the system in accordance with an embodiment that combines the features of the systems shown in FIGS. 10 and 12 to enable biomimetic processing of biological inputs in order to generate control signals for controlling the VR prosthesis system or the prosthesis device.

FIG. 13 is a block diagram of the system 130 in accordance with an embodiment that combines the features of the systems 100 and 120 shown in FIGS. 10 and 12, respectively, to enable biomimetic processing of biological inputs in order to generate control signals for controlling the VR prosthesis system 108 or the prosthesis device 106. In accordance with this representative embodiment, the system 130 includes a switching device 131 comprising first and second switching elements 131a and 131b, respectively. In a first switching configuration of the switching device 131, the first switching element 131a interconnects the prosthesis controller 105 with the VR system 108 and the second switching element 131b interconnects the musculoskeletal model 103 with the Poly block 104. This causes the system 130 to operate in the manner described above with reference to FIG. 12. In a second switching configuration of the switching device 131, the first switching element 131a interconnects the prosthesis controller 105 with the prosthesis device 106 and the second switching element 131b interconnects the prosthesis device 106 with the Poly block 104. This causes the system 130 to operate in the manner described above with reference to FIG. 10.

Figure 14:
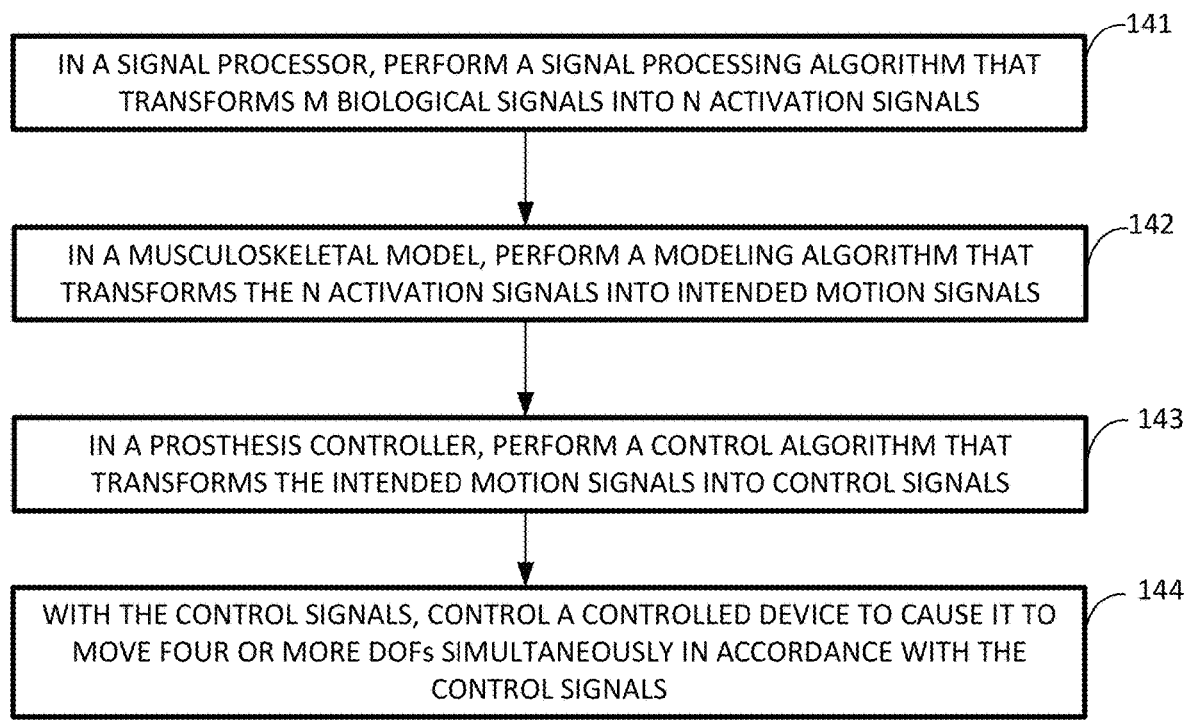
FIG. 14 is a flow diagram depicting the method in accordance with a representative embodiment.

FIG. 14 is a flow diagram depicting the method in accordance with a representative embodiment. With reference to block 141, a signal processor of a mimetic controller, a signal processing algorithm is performed that processes M biological signals received from a residual limb at an input port of the signal processor to transform the M biological signals into N activation signals, where M and N are integers and M is less than N, the N activation signals being outputted from the output port. With reference to block 142, a musculoskeletal model of the mimetic controller performs a modeling algorithm that transforms the N activation signals received at an input port of the musculoskeletal model into intended motion signals and outputs the intended motion signals from an output port of the musculoskeletal model. With reference to block 143, a prosthesis controller of the system performs a control algorithm that transforms the intended motion signals received at an input port of the prosthesis controller into control signals that are outputted from an output port of the prosthesis controller. With reference to block 144, a controlled device receives the control signals and moves four or more DOFs simultaneously in accordance with the control signals. Direct control of four or more DOFs can mean, but is not limited to, hand opening and closing in a power grip with simultaneous flexion or extension of the wrist end rotation of the wrist.

It should be noted that although the inventive principles and concepts disclosed herein have been described with reference the prosthesis controller 105 controlling a prosthesis device 106 (e.g., a prosthetic limb) or a VR prosthesis system 108, the controlled device may be other types of devices such as, for example, active assistive devices (e.g. exoskeletons, muscle stimulation systems, etc.), computer interface devices (e.g., game controllers, gesture-based interactive systems, etc.), and other peripherals (e.g., drones, robotic devices, etc.).

As indicated above, the four or more control signals cause the controlled device to move that many or fewer DOFs of the prosthesis or other device under the direct and simultaneous control of the biological signals. For example, the control signals can cause the controlled device to perform one or more tasks with at least four DOFs with a loop time that is less than 2 ms.

Figure 15:
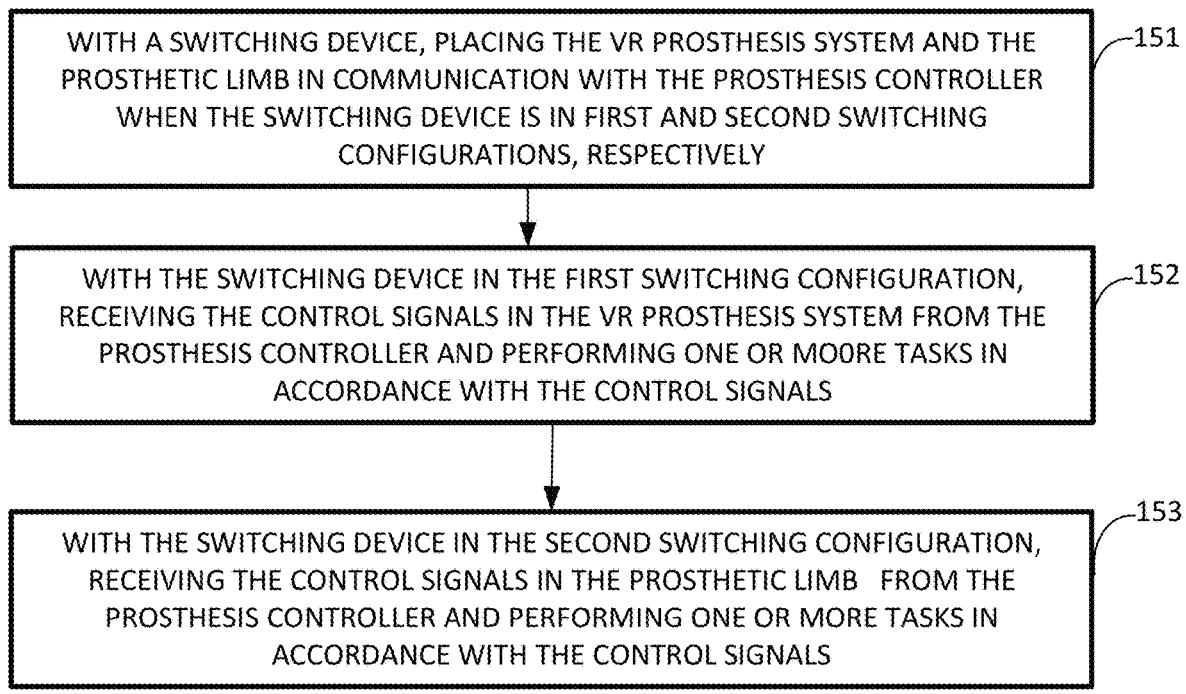
FIG. 15 is a flow diagram of modifications to the method represented by the flow diagram of FIG. 14 for the case where the controlled device referred to in step 144 is a VR prosthesis system or a prosthetic limb.

FIG. 15 is a flow diagram of modifications to the method represented by the flow diagram of FIG. 14 for the case where the controlled device referred to in step 144 is a VR prosthesis system or a prosthetic limb. With a switching device of the system, placing the VR prosthesis system and the prosthetic limb in communication with the prosthesis controller when the switching device is in first and second switching configurations, respectively, as indicated by block 151. With the switching device in the first switching configuration, the VR prosthesis system receives the control signals from the prosthesis controller and performs one or more tasks in accordance with the control signals, as indicated by block 152. With the switching device is in the second switching configuration, the prosthetic limb receives the control signals from the prosthesis controller and performs one or more tasks in accordance with the control signals, as indicated by block 153.

Figure 16:
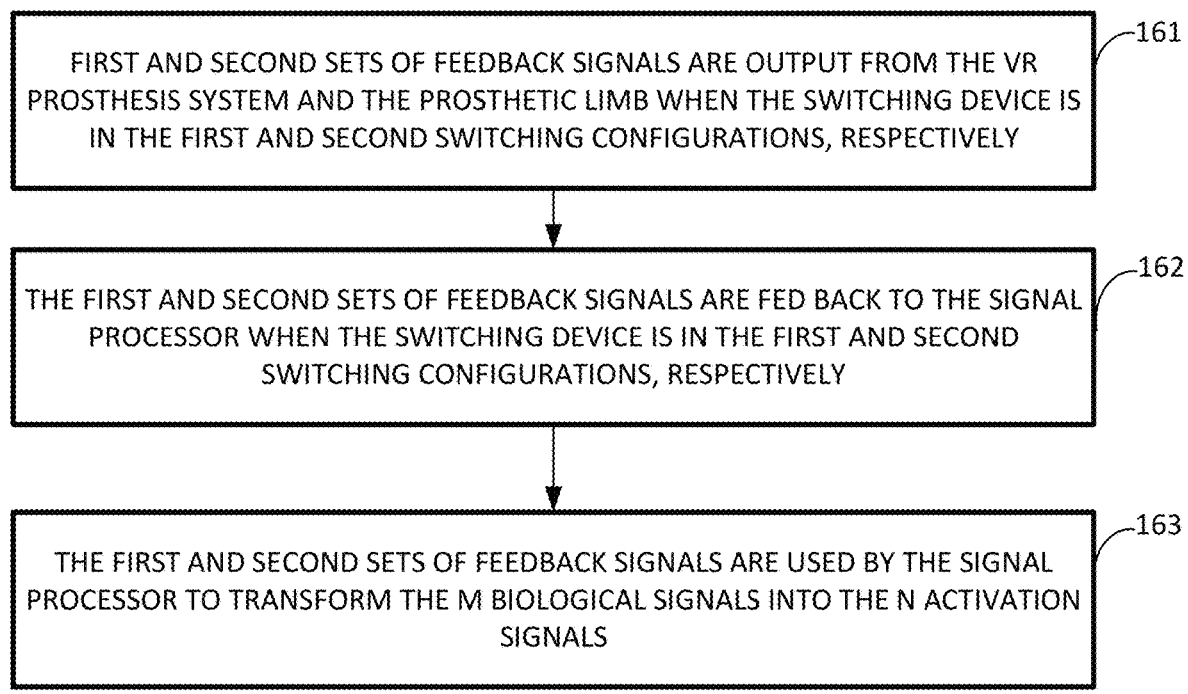
FIG. 16 is a flow diagram of modifications to the method represented by the flow diagram of FIG. 15 in accordance with an embodiment.

FIG. 16 is a flow diagram in accordance with a representative embodiment in which the method represented by the flow diagram of FIG. 15 further comprises the following. First and second sets of feedback signals are output from the VR prosthesis system and the prosthetic limb, respectively, when the switching device is in the first and second switching configurations, respectively, as indicated by block 161. Each of the first and second sets of feedback signals describes a virtual motion within the VR prosthesis system and an actual motion of the prosthetic limb, respectively. With reference to block 162, the first and second sets of feedback signals are fed back to the signal processor when the switching device is in the first and second switching configurations, respectively. With reference to block 163, the first and second sets of feedback signals are used by the signal processor to transform the M biological signals into the N activation signals.

Figure 17:
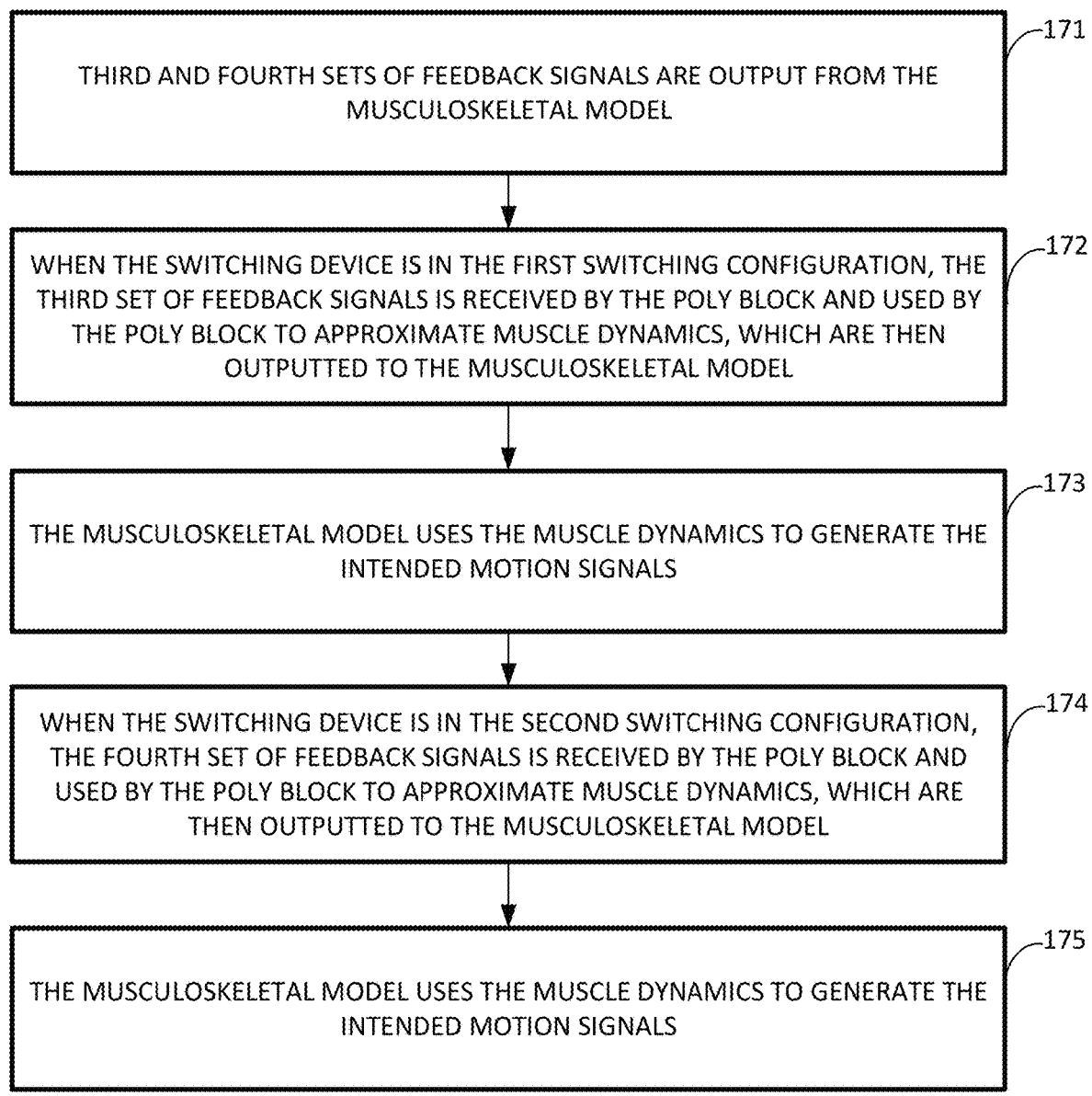
FIG. 17 is a flow diagram of modifications to the method represented by the flow diagram of FIG. 16 in accordance with an embodiment.

FIG. 17 is a flow diagram in accordance with a representative embodiment in which the method represented by the flow diagram of FIG. 16 further comprises the following. With reference to block 171, third and fourth sets of feedback signals are output from the musculoskeletal model and the prosthetic limb, respectively. With a Poly block of the mimetic controller, when the switching device is in the first switching configuration, the third set of feedback signals is received and used by the Poly block to approximate muscle dynamics that are outputted to the musculoskeletal model, as indicated by block 172. With reference to block 173, the approximated muscle dynamics are used by the musculoskeletal model to generate the intended motion signals. With reference to block 174, when the switching device is in the second switching configuration, the fourth set of feedback signals is received in the Poly block from the prosthetic limb and used by the Poly block to approximate muscle dynamics that are outputted to the musculoskeletal model. With reference to block 175, the muscle dynamics are used by the musculoskeletal model to generate the intended motion signals.

The methods described above are typically implemented in software, firmware, or a combination thereof, executed on one or more processors, controllers or computers. Alternatively, the methods may be implemented solely in hardware, such as a state machine or an application specific integrated circuit (ASIC), for example. The software, firmware, or combination thereof, is stored in one or more memory devices that may be part of the biomimetic controller 101 or the prosthesis controller 105, depending on which part of the method is being performed.

Figure 18A:
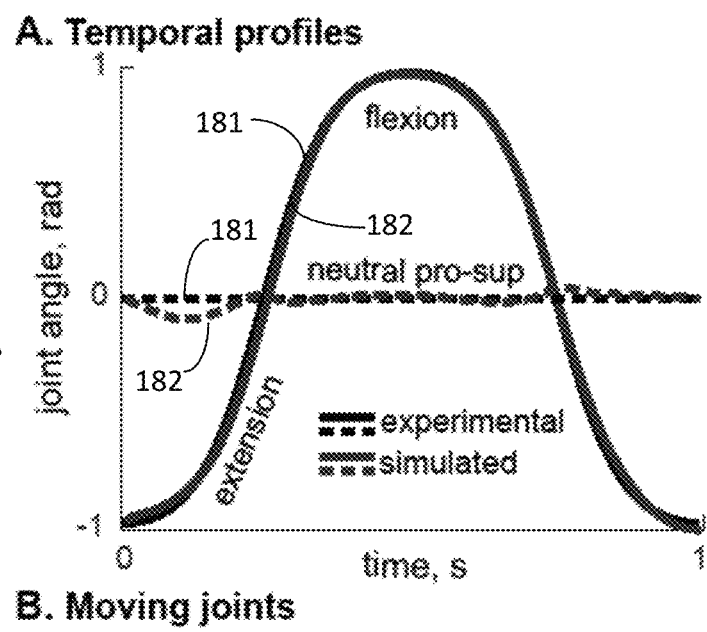
FIGS. 18A-18C are graphs demonstrating multi-dimensional control of a controlled device, e.g., a prosthetic limb, by the systems shown in FIGS. 10, 12 and 13 in accordance with a representative embodiment.
Figure 18B:
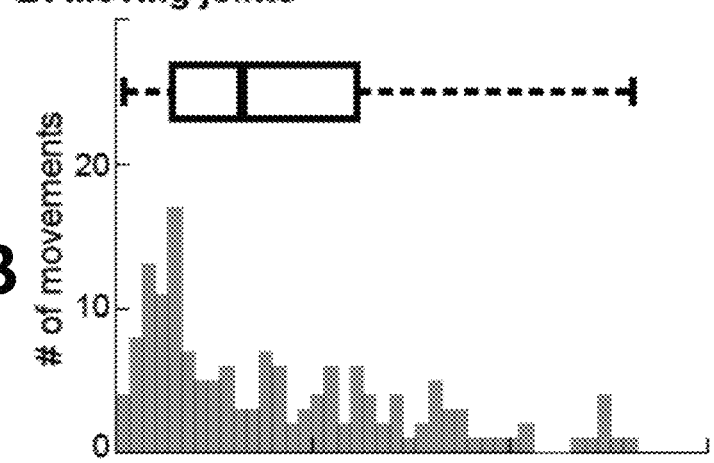
Figure 18C:
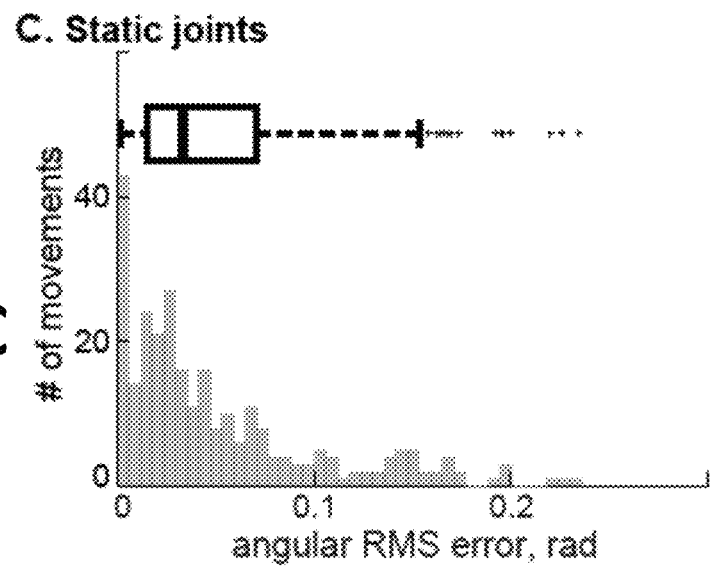

FIGS. 18A-18C are graphs demonstrating multi-dimensional control of a controlled device, e.g., a prosthetic limb, by the systems shown in FIGS. 10, 12 and 13 in accordance with a representative embodiment. FIG. 18A shows an example of experimental and simulated temporal profiles 181 and 182, respectively, of a hand movement, where the wrist was flexed then extended through the whole range of motion without pronating or supinating (i.e., neutral pronation and supination (pro-sup)) and with fingers extended. These movements involved 18 DOF of the hand. EMG-driven real-time simulations reproduced the recorded experimental motion very closely. FIGS. 18B and 18C demonstrate the performance across multiple hand movements, such as palm up and down, wrist flex and extend, fingers flex and extend, and similar movements. The angular root mean squared (RMS) error between simulated and recorded motions was very low for both moving joints (FIG. 18B) and static joints that were not moving but had to be held still with active forces (FIG. 18C).

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure.

For example, while the inventive principles and concepts have been described herein with reference to controlling a prosthetic 50, the described software and/or firmware can be used in other applications that require fast and memory-efficient approximation of complex multidimensional data, such as, for example, with robots or autonomous drones controlled by small chips that need to approximate information about interactions with objects or terrain, that are originally calculated using systems of differential equations.

What is claimed is:

1. A system comprising:
  a biomimetic controller comprising:
   a signal processor configured to perform a signal processing algorithm that processes M biological signals received from a subject in the signal processor to transform the M biological signals into N activation signals, where M and N are integers and M is less than N, the N activation signals being outputted from the signal processor, and
   a musculoskeletal model that receives the N activation signals, the musculoskeletal model being configured to perform a modeling algorithm that transforms the N activation signals into intended motion signals, the intended motion signals being outputted from the musculoskeletal model;
  a controller that receives the intended motion signals, the controller being configured to perform a control algorithm that transforms the intended motion signals into control signals that are outputted from the controller; and
  a controlled device in communication with the controller, the controlled device receiving the control signals and performing one or more tasks in accordance with the control signals.

2. The system of claim 1, wherein the control signals cause the controlled device to perform said one or more tasks with a number of degrees of freedom (DOFs), and wherein the number of DOFs is greater than or equal to three.

3. The system of claim 2, wherein the control signals cause the controlled device to perform said one or more tasks with at least four DOFs with a loop time that is less than 2 milliseconds (ms).

4. The system of claim 1, wherein the controlled device is an active assistive device selected from a list comprising an exoskeleton system and a muscle stimulation system.

5. The system of claim 1, wherein the controlled device is a computer interface device selected from a list comprising a gesture-based interactive system.

6. The system of claim 1, wherein the controlled device is a virtual reality (VR) prosthesis system.

7. The system of claim 1, wherein the controlled device is a prosthetic limb.

8. The system of claim 1, wherein the controlled device comprises one of a virtual reality (VR) prosthesis system and a prosthetic limb, the system further comprising:
  a switching device, the VR prosthesis system and the prosthetic limb being in communication with the controller via the switching device when the switching device is in first and second switching configurations, respectively, wherein when the switching device is in the first switching configuration, the VR prosthesis system receives the control signals from the controller and performs said one or more tasks in accordance with the control signals, and wherein when the switching device is in the second switching configuration, the prosthetic limb receives the control signals from the controller to perform said one or more tasks in accordance with the control signals.

9. The system of claim 8, wherein first and second sets of feedback signals are output from the VR prosthesis system and the prosthetic limb, respectively, when the switching device is in the first and second switching configurations, respectively, each of the first and second sets of feedback signals describing a virtual motion within the VR prosthesis system and an actual motion of the prosthetic limb, respectively, the first and second sets of feedback signals being fed back to the signal processor when the switching device is in the first and second switching configurations, respectively, and being used by the signal processor to transform the M biological signals into the N activation signals.

10. The system of claim 9, wherein third and fourth sets of feedback signals are output from the musculoskeletal model and the prosthetic limb, respectively, and wherein the biomimetic controller further comprises:
  a polynomial approximation (Poly) block, the Poly block being in communication with the output of the musculoskeletal model when the switching device is in the first switching configuration to receive the third set of feedback signals, the Poly block being in communication with the prosthetic limb when the switching device is in the second switching configuration to receive the fourth set of feedback signals from the prosthetic limb, the Poly block using the third and fourth sets of feedback signals when the switching device is in the first and second switching configurations, respectively, to approximate muscle dynamics that are outputted to the musculoskeletal model and used by the musculoskeletal model to generate the intended motion signals.

11. The system of claim 8, further comprising:
  at least one instrumented object in communication with the VR prosthesis system and the prosthetic limb, said at least one instrumented object measuring motions of virtual objects that are manipulated by the VR prosthesis system when the switching device is in the first switching configuration and outputting a first set of feedback signals, said at least one instrumented object measuring motions of real or virtual objects that are manipulated by the prosthetic limb when the switching device is in the second switching configuration and outputting a second set of feedback signals, the first and second sets of feedback signals being fed back to the signal processor and used by the signal processor to transform the M biological signals into the N activation signals.

12. A method for controlling a device comprising:
  with a signal processor of a mimetic controller performing a signal processing algorithm that processes M biological signals received from a subject in the signal processor to transform the M biological signals into N activation signals, where M and N are integers and M is less than N, the N activation signals being outputted from the signal processor;
  with a musculoskeletal model of the mimetic controller, receiving the N activation signals and performing a modeling algorithm that transforms the N activation signals into intended motion signals and output the intended motion signals from the musculoskeletal model;
  with a controller of the system, receiving the intended motion signals and performing a control algorithm that transforms the intended motion signals into control signals that are outputted from the controller; and
  with a controlled device in communication with the controller, receiving the control signals and performing one or more tasks in accordance with the control signals.

13. The method of claim 12, wherein the control signals cause the controlled device to perform said one or more tasks with a number of degrees of freedom (DOFs), and wherein the number of DOFs is greater than or equal to three.

14. The method of claim 13, wherein the control signals cause the controlled device to perform said one or more tasks with at least four DOFs with a loop time that is less than 2 milliseconds (ms).

15. The method of claim 12, wherein the controlled device is an active assistive device selected from a list comprising an exoskeleton system and a muscle stimulation system.

16. The method of claim 12, wherein the controlled device is a computer interface device selected from a list comprising a gesture-based interactive system.

17. The method of claim 12, wherein the controlled device is a virtual reality (VR) prosthesis system.

18. The method of claim 12, wherein the controlled device is a prosthetic limb.

19. The method of claim 12, wherein the controlled device comprises one of a virtual reality (VR) prosthesis system and a prosthetic limb, the method further comprising:
  with a switching device of the system, placing the VR prosthesis system and the prosthetic limb in communication with the controller when the switching device is in first and second switching configurations, respectively, wherein when the switching device is in the first switching configuration, the VR prosthesis system receives the control signals from the controller and performs said one or more tasks in accordance with the control signals, and wherein when the switching device is in the second switching configuration, the prosthetic limb receives the control signals from the controller to perform said one or more tasks in accordance with the control signals.

20. The method of claim 19, wherein first and second sets of feedback signals are output from the VR prosthesis system and the prosthetic limb, respectively, when the switching device is in the first and second switching configurations, respectively, each of the first and second sets of feedback signals describing a virtual motion within the VR prosthesis system and an actual motion of the prosthetic limb, respectively, the method further comprising:
  feeding back the first and second sets of feedback signals to the signal processor when the switching device is in the first and second switching configurations, respectively; and
  in the signal processor, using the first and second sets of feedback signals to transform the M biological signals into the N activation signals.

21. The method of claim 20, wherein third and fourth sets of feedback signals are output from the musculoskeletal model and the prosthetic limb, respectively, and wherein the method further comprises:
  with a polynomial approximation (Poly) block of the mimetic controller, the Poly block being in communication with the output of the musculoskeletal model when the switching device is in the first switching configuration, receiving the third set of feedback signals and using the third set of feedback signals to approximate muscle dynamics that are outputted to the musculoskeletal model and used by the musculoskeletal model to generate the intended motion signals; and
  with the Poly block, the Poly block being in communication with the prosthetic limb when the switching device is in the second switching configuration, receiving the fourth set of feedback signals from the prosthetic limb and using the fourth set of feedback signals to approximate muscle dynamics that are outputted to the musculoskeletal model and used by the musculoskeletal model to generate the intended motion signals.

* * * * *